US 8,021,813 B2

(12) United States Patent
Sato et al.

(10) Patent No.: US 8,021,813 B2
(45) Date of Patent: Sep. 20, 2011

(54) ELECTROSTATIC-IMAGE-DEVELOPING TONER, METHOD OF PRODUCING THE SAME, ELECTROSTATIC IMAGE DEVELOPER, IMAGE FORMING METHOD AND IMAGE FORMING APPARATUS

(75) Inventors: Shuji Sato, Kanagawa (JP); Eisuke Iwazaki, Kanagawa (JP); Atsushi Sugawara, Kanagawa (JP); Masanobu Ninomiya, Kanagawa (JP); Hiroshi Nakazawa, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 147 days.

(21) Appl. No.: 12/335,267

(22) Filed: Dec. 15, 2008

(65) Prior Publication Data

US 2009/0274972 A1 Nov. 5, 2009

(30) Foreign Application Priority Data

May 1, 2008 (JP) .................................. 2008-119644

(51) Int. Cl.
*G03G 9/16* (2006.01)
(52) U.S. Cl. .................................. 430/108.1; 430/137.1
(58) Field of Classification Search ............... 430/108.1, 430/137.1
See application file for complete search history.

(56) References Cited

U.S. PATENT DOCUMENTS

| 3,964,903 | A | * | 6/1976 | Van Besauw et al. ..... 430/108.3 |
| 4,085,057 | A | * | 4/1978 | Masuda et al. ........... 430/108.21 |
| 4,108,786 | A | * | 8/1978 | Takayama et al. ......... 430/106.2 |
| 2005/0255402 | A1 | | 11/2005 | Hopper et al. |
| 2007/0042286 | A1* | | 2/2007 | Vanbesien et al. ....... 430/137.14 |
| 2007/0108097 | A1 | | 5/2007 | Patel et al. |
| 2007/0111127 | A1 | | 5/2007 | Patel et al. |
| 2007/0111128 | A1 | | 5/2007 | Patel et al. |
| 2007/0111131 | A1 | | 5/2007 | Patel et al. |
| 2007/0131580 | A1 | | 6/2007 | Patel et al. |
| 2007/0238040 | A1 | | 10/2007 | Veregin et al. |

FOREIGN PATENT DOCUMENTS

| JP | A-10-161352 | 6/1998 |
| JP | A-10-319804 | 12/1998 |
| JP | A-2000-56512 | 2/2000 |
| JP | A-2001-117264 | 4/2001 |
| JP | B2-3264218 | 12/2001 |
| JP | A-2005-18058 | 1/2005 |
| JP | A-2007-138167 | 6/2007 |
| JP | A-2007-138168 | 6/2007 |
| JP | A-2007-140517 | 6/2007 |
| JP | A-2007-140518 | 6/2007 |
| JP | A-2007-140519 | 6/2007 |
| JP | A-2007-279726 | 10/2007 |
| JP | A-2008-40319 | 2/2008 |

OTHER PUBLICATIONS

Apr. 6, 2010 Office Action issued in Japanese Patent Application No. 2008-119644 (with translation).

* cited by examiner

*Primary Examiner* — Hoa V Le
(74) *Attorney, Agent, or Firm* — Oliff & Berridge, PLC

(57) ABSTRACT

An electrostatic-image-developing toner includes a phosphonic acid based sequestering agent.

7 Claims, No Drawings

ELECTROSTATIC-IMAGE-DEVELOPING TONER, METHOD OF PRODUCING THE SAME, ELECTROSTATIC IMAGE DEVELOPER, IMAGE FORMING METHOD AND IMAGE FORMING APPARATUS

CROSS-REFERENCE TO RELATED APPLICATIONS

This application is based on and claims priority under 35 USC 119 from Japanese Patent Application No. 2008-119644 filed on May 1, 2008.

BACKGROUND

1. Technical Field

This invention relates to an electrostatic-image-developing toner, a method of producing the same, an electrostatic image developer, an image forming method and an image forming apparatus.

2. Related Art

In an image forming apparatus of the so-called xerography type, which has a latent image holding member (an electrophotographic photoreceptor (hereinafter sometimes referred to as "a photoreceptor"), a charging device, an exposing device, a development device and a transfer device, an image is formed via an electrophotographic process using these devices.

Owing to the technical advances in the individual members and systems in recent years, these xerographic image forming apparatuses have been advancing from the view points of high-speed image forming, high-quality images and long life time. Along with this trend, there are even greater demands than before for the applicability to high speed processing, and for the high reliability, of each of the subsystems. In particular, the demands for high speed applicability and high reliability are even greater for photoreceptors to be used in writing images thereon, and cleaner for cleaning the photoreceptors. Further, they are subjected to larger stress from the sliding motion between them than other members and thus readily suffer from scratches and abrasion, which sometimes results in image defects.

With the expansion of the life time of systems, on the other hand, there are also strong demands for improvement in durability and stabilization of electrical characteristics of toner particles located between contact type charging members. However, such improvement in durability and stabilization of electrical characteristics of toner particles conflict with a decrease in toner viscosity and an increase in the elasticity thereof aiming at saving energy. Thus, it has been becoming difficult to establish both of these purposes.

SUMMARY

According to an aspect of the invention, there is provided an electrostatic-image-developing toner including a phosphonic acid based sequestering agent.

DETAILED DESCRIPTION (Electrostatic-image-developing Toner)

The electrostatic-image-developing toner (hereinafter sometimes referred to simply as "toner") in the present exemplary embodiment is characterized by containing a phosphonic acid based sequestering agent.

The inventors have found out that by blending a phosphonic acid based sequestering agent into a toner, the dispersibility of coloring agent particles, mold releasing agent particles and so on contained in the toner can be improved, thereby completing the invention. It is preferable that the sequestering agent having a specific element as described above (phosphonic acid based sequestering agent) is used as a mixture with a coloring agent dispersion or a mold releasing agent dispersion. Thus, it has been clarified that impurity ions can be effectively sequestered in the course of particularization so that not only impurities on the surface but also internal impurities can be removed thereby.

In this exemplary embodiment, the electrostatic-image-developing toner is prepared by adding, if necessary, an external additive to toner matrix particles. Therefore, the term "toner matrix particles" means toner particles from which the external additive has been removed or toner particles before the addition of the external additive.

Next, this exemplary embodiment will be illustrated in greater detail.

First, the phosphonic acid based sequestering agent that is the characteristic component of the electrostatic-image-developing toner of this exemplary embodiment will be illustrated.

<Phosphonic Acid Based Sequestering Agent>

In this exemplary embodiment, the phosphonic acid based sequestering agent is not particularly restricted and thus a publicly known phosphonic acid based sequestering agent can be appropriately selected and employed.

The phosphonic acid based sequestering agent is not particularly restricted so long as it is a compound capable of forming a salt or a complex together with an ionic impurity such as a metal ion in the course of producing an electrostatic-image-developing toner. That is, it is not particularly restricted so long as having a phosphonate group or its salt (complex). As the electrostatic-image-developing toner in the exemplary embodiment, namely, use may be made of an electrostatic-image-developing toner that is produced by using a phosphonic acid based sequestering agent. After the production, the phosphonic acid based sequestering agent may undergo salt formation or complex formation.

As an example of the phosphonate group or its salt carried by the phosphonic acid based sequestering agent in the course of producing the toner, the following partial structure can be presented.

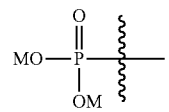

In the chemical formula 3, M represents a hydrogen atom, an alkali metal atom (for example, a sodium atom, a potassium atom or a lithium atom) or a quaternary ammonium (for example, ammonium, pyridinium, triethanolammonium or triethylammonium).

In the exemplary embodiment, it is preferable that the phosphonic acid based sequestering agent is a compound which has two or more phosphonate groups and/or salts thereof per molecule (a polyphosphonic acid compound) or at least one phosphonate group and/or its salt together with one or more carboxylate groups and/or salts thereof (a phosphonocarboxylic acid compound).

Examples of the polyphosphonic acid compound include polyphosphonic acids such as ethane-1,1-diphosphonic acid, ethane-1,1,2-triphosphonic acid, ethane-1-hydroxy-1,1-diphosphonic acid (1-hydroxyethylidene-1,1-diphosphonic acid), ethanehydroxy-1,1,2-triphosphonic acid, ethane-1,2-dicarboxy-1,2-diphosphonic acid and methanehydroxy-diphosphonic acid, and alkali metal salts or quaternary ammonium salts thereof.

As the polyphosphonic acid compound, it is also possible to use an aminopolyphosphonic acid compound, for example, amino polyphosphonic acids such as aminotri(methylenephosphonic acid), ethylenediamine tetramethylenephosphonic acid) and ethylenetriamine penta(methylenephosphonic acid), and alkali metal salts or quaternary ammonium salts thereof.

Examples of the phosphonocarboxylic acid compound include phosphonocarboxylic acids such as 2-phosphonobutane-1,2-dicarboxylic acid, 1-phosphonobutane-2,3,4-tricarboxylic acid and α-methylphosphonosuccinic acid, and alkali metal salts or quaternary ammonium salts thereof.

Moreover, use can be made of a polyaminopolycarboxylic acid having at least four phosphonate groups (or salts thereof) that is disclosed in JP-A-2000-147729 and phosphonocarboxylic acids represented by the formula I that is disclosed in JP-A-4-265200.

In this exemplary embodiment, it is preferable that the phosphonic acid based sequestering agent is soluble in water under acidic conditions. This is because a phosphonic acid based sequestering agent being soluble in water under acidic conditions would not separate out in the case of producing the electrostatic-image-developing toner of the exemplary embodiment by forming aggregated particles under acidic conditions, which makes the phosphonic acid based sequestering agent suitably usable in the chemical production method (aggregation/coalescence method) as will be described hereinafter. In the case where no separation occurs, it is preferable to employ acidic conditions under which the hydrophobicities on the toner particle surface and inside thereof are increased and thus the phosphonic acid based sequestering agent is selectively adsorbed and effectively offer the function thereof.

Among these phosphonic acid based sequestering agents it is appropriate in the exemplary embodiment to use a compound represented by the following formula (1) and/or formula (2). It is preferable that the electrostatic-image-developing toner in the exemplary embodiment is an electrostatic-image-developing toner produced by using a phosphonic acid based sequestering agent represented by the following formula (1) and/or formula (2). After the production, the phosphonic acid based sequestering agent may undergo salt formation or complex formation.

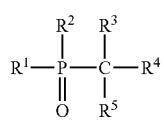

(1)

In the formula (1), each of $R^1$ and $R^2$ represents —OM wherein M represents a hydrogen atom, an alkali metal or a quaternary ammonium. Each of $R^3$, $R^4$ and $R^5$ independently represents a hydroxyl group, a carboxyl group, an alkyl or alkenyl group optionally having a hydroxyl or carboxyl group at the terminal thereof, or $NR^{12}R^{13}$ wherein each of $R^{12}$ and $R^{13}$ independently represents a hydrogen atom, an alkyl group, an alkenyl group or an acyl group, and $R^{12}$ and $R^{13}$ may be bonded together to form a ring. $R^1$ and $R^2$ may be the same as or different from each other.

The alkyl and alkenyl groups ($R^3$ to $R^5$, $R^{12}$ and $R^{13}$) may have a substituent other than the hydroxyl group and the carboxyl group. Examples of the substituent include a phosphonate group and alkoxy groups having from 1 to 6 carbon atoms.

It is preferable that the alkyl and alkenyl group have each from 1 to 10 carbon atoms, more preferably from 1 to 5 carbon atoms.

It is preferable that each of $R^3$, $R^4$ and $R^5$ represents a hydroxyl group, a carboxyl group or an alkyl group optionally having a hydroxyl or carboxyl group at the terminal thereof.

In the formula (1), it is preferred that at least one of $R^3$ to $R^5$ has a carboxyl group or a phosphonate group and having a carboxyl group is still preferred. The carboxyl group or the phosphonate group may form a salt. Examples of the salt thus formed include a sodium salt, a potassium salt, a lithium salt and a quaternary ammonium salt.

In the formula (1), it is preferable that $R^3$ to $R^5$ are each a carboxyl group or an alkyl group having a carboxyl group at the terminal thereof. It is particularly preferable that the alkyl group has 1 to 5 carbon atoms.

As specific examples of the compound represented by the formula (1), there can be enumerated 2-phosphonobutane-1,2,4-tricarboxylic acid (PBTC) and its salt.

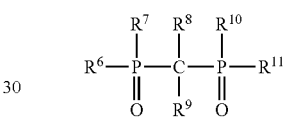

(2)

In the formula (2), each of $R^6$, $R^7$, $R^{10}$ and $R^{11}$ represents —OM wherein M represents a hydrogen atom, an alkali metal or a quaternary ammonium. Each of $R^8$ and $R^9$ independently represents a hydrogen atom, a hydroxyl group, an alkyl group, an alkenyl group or $NR^{12}R^{13}$ wherein each of $R^{12}$ and $R^{13}$ independently represents a hydrogen atom, an alkyl group, an alkenyl group or an acyl group, or $R^{12}$ and $R^{13}$ may be bonded together to form a ring. $R^6$, $R^7$, $R^{10}$, and $R^{11}$ may be the same as or different from each other.

The alkyl and alkenyl groups ($R^8$, $R^9$, $R^{12}$ and $R^{13}$) may have a substituent and examples of the substituent include a phosphonate group and alkoxy groups having from 1 to 6 carbon atoms. In the case where $R^{12}$ and $R^{13}$ are bonded together to form a ring, the ring thus formed may be a heterocyclic ring including —O—, —S—, —$NR^{13}$— or the like. It is preferable that the alkyl group and the alkenyl group have each 1 to 10 carbon atoms, more preferably 1 to 5 carbon atoms. $R^{13}$ has the same meaning as $R^{12}$ in the formula (2).

In the above formulae (1) and (2), it is preferable that M is a hydrogen atom, sodium or potassium, more preferably a hydrogen atom or sodium and still more preferably a hydrogen atom.

In the formula (2), it is preferable either $R^8$ or $R^9$ is a hydroxyl group. That is, a compound represented by the formula (3) is preferred as the compound represented by the formula (2).

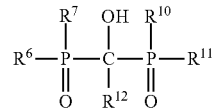

(3)

In the formula (3), $R^6$, $R^7$, $R^{10}$ and $R^{11}$ respectively have the same meanings as in the formula (2) and preferred ranges thereof are also the same.

In the formula (3), $R^{12}$ is a substituted or unsubstituted alkyl group having 1 to 5 carbon atoms. Preferable examples thereof include a methyl group, a methoxymethyl group, an ethyl group, an isopropyl group, an n-butyl group, a t-butyl group and an n-pentyl group. $R^{12}$ is preferably a methyl or ethyl group and an ethyl group is most preferred. As examples of the substituent, alkoxy groups having 1 to 6 carbon atoms may be cited.

Specific examples of the compound represented by the formula (3) include 1-hydroxyethylidene-1,1-diphosphonic acid (HEDP), 1-hydroxy-n-propylidene-1,1-diphosphonic acid, 1-hydroxy-2,2-dimethylpropylidene-1,1-diphosphonic acid and alkali metal salts and ammonium salts thereof.

The phosphonic acid based sequestering agents represented by the above formulae (1) and (2) are preferable, since they are excellent in solubility and stability under acidic conditions and, therefore, well sequester ionic impurities in the course of producing a toner to ensure uniform dispersion of coloring agent particles and mold releasing agent particles. Moreover, they can be particularly appropriately employed because of having an effect of reducing scales by preventing thickening.

There can be enumerated commercially available phosphonic acid based sequestering agents such as CHELEST PH-210 (1-hydroxyethylidene-1,1-diphosphonic acid; HEDP), CHELEST PH-430 (2-phosphonobutane-1,2,4-tricarboxylic acid; PBTC), CHELEST PH-320 (nitrilotris(m-ethylenephosphonic acid (aminotri(methylenephosphonic acid); NTMP) and CHELEST PH540 (N,N,N',N'-tetrakis (phosphonomethyl)ethylenediamine; EDTMP).

Next, specific examples of the phosphonic acid based sequestering agent will be presented, though the exemplary embodiment is not restricted thereto. In the following exemplary compounds, each phosphonic acid based sequestering agent may be in the form of an alkali metal salt or a quaternary ammonium salt.

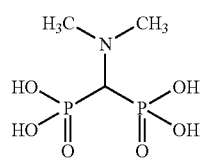
(A-1)

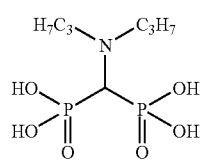
(A-2)

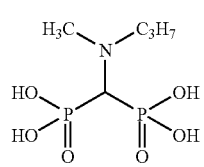
(A-3)

-continued

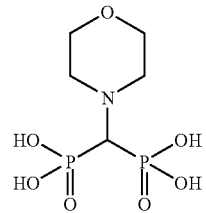
(A-4)

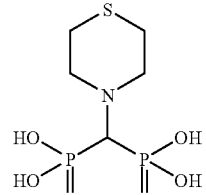
(A-5)

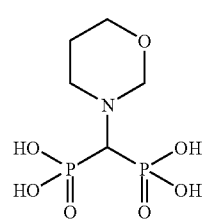
(A-6)

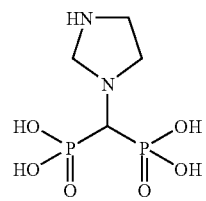
(A-7)

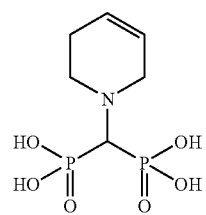
(A-8)

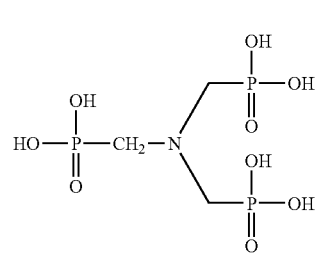
(A-9)

(A-10)

(A-11) 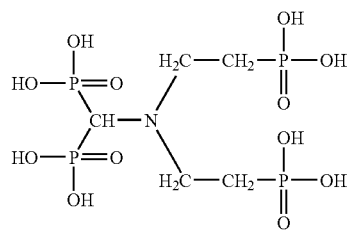

(A-12) 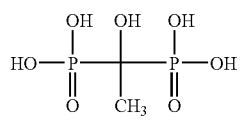

(A-13) 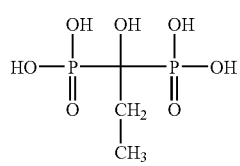

(A-14) 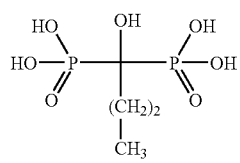

(A-15) 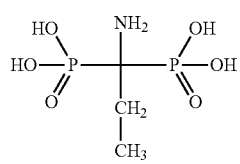

(A-16) 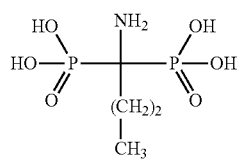

(A-17) 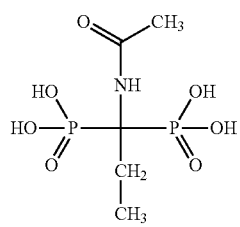

(A-18) 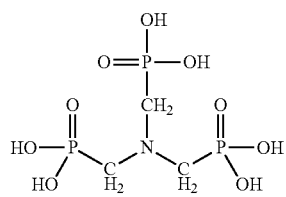

(A-19) 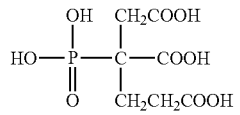

(A-20) 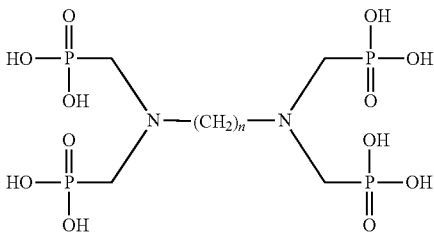

$n = 1\text{-}8$ (A-21) 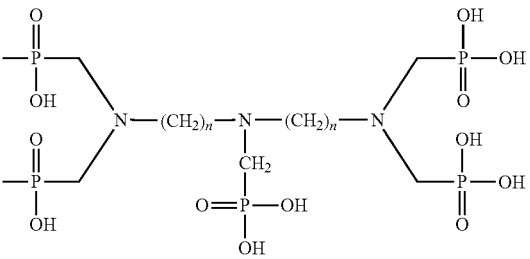

$n = 1\text{-}8$

Among the exemplary compounds as cited above, (A-9), (A-12), (A-13), (A-14), (A-15), (A-19) and salts thereof may be enumerated as preferred examples. (A-12), (A-19) and salts thereof are more preferred.

In this exemplary embodiment, either one phosphonic acid based sequestering agent or a combination of two or more kinds of phosphonic acid based sequestering agents may be used. It is preferable that the toner of the exemplary embodiment contains at least one of the phosphonic acid based sequestering agents represented by the formula (1) and/or the formula (2).

In the exemplary embodiment, the content of the phosphonic acid based sequestering agent is preferably 0.1% by weight or more but not more than 10% by weight (in the exemplary embodiment, "0.1% by weight or more but not more than 10% by weight" is expressed as "0.1 to 10% by weight" or "0.1% by weight to 10% by weight"; the same applies hereinafter), more preferably 0.3 to 7% by weight and still more preferably 0.5 to 5% by weight, based on the total weight of the entire toner matrix particles.

It is preferable that the phosphonic acid based sequestering agent content falls within the range as specified above, since metal ions can be effectively sequestered and the performance-holding properties are improved thereby so that a high quality image can be formed over a long period of time.

The phosphonic acid based sequestering agent content as described above means the ratio to the entire toner matrix particles. However, it is more preferable that the toner of the exemplary embodiment contains the phosphonic acid based sequestering agent with a distribution over the surface and inside of the same, as will be described in detail hereinafter.

<Amount of Phosphorus Element>

In the present exemplary embodiment, it is preferable that, when the ratio of the intensity of phosphorus element to the total intensity of all elements detected in the toner by the fluorescent X-ray analysis is referred to as A and the ratio of the intensity of phosphorus element to the total intensity of all elements detected in the toner having been dispersed in an alcoholic solvent followed by drying, by the fluorescent X-ray analysis is referred to as B, the following requirements are satisfied:

$$0.05 \leq A \leq 0.5$$

$$0.40 \leq B/A \leq 0.75.$$

Although the phosphorus element as described above is supposed as the phosphorus element originating in the phosphonic acid based sequestering agent, the occurrence of phosphorus element not originating in the phosphonic acid based sequestering agent is not excluded.

As the results of the inventors' studies on the amount of the phosphonic acid based sequestering agent existing within the toner and in the neighborhood of the surface, it is found out that the exposure of a coloring agent, a mold releasing agent and so on the surface can be prevented and thus a toner having excellent internal dispersion properties can be obtained by measuring the amount of phosphorus element as an indication by the fluorescent X-ray analysis and regulating the amount within a specific range. Thus, it becomes possible to prevent the deposition of toner components on the photoreceptor surface so that the life time of the system can be extended and improved image qualities can be established even in the case of using an electrostatic latent image holding member (a photoreceptor) having a long-life protective layer.

In the case where the amount of the phosphonic acid based sequestering agent existing in the neighborhood of the toner surface and the inside thereof is smaller than a definite level, the dispersibilities of coloring agent particles and mold releasing agent particles in the toner are sometimes lowered, though there arises no serious problem such as an image defect during a short time use. As a result, it is sometimes observed that these particles are largely localized in the neighborhood of the surface. When the stress loaded on toner particles due to the above phenomenon during a long time use, there frequently arise problems such as filming in the localized area on the photoreceptor surface, embodiment of the external additives and streaking caused by the localization of the external additives. The tendency of lowering the dispersibilities in the toner becomes further apparent with an increase in the amount of the coloring agent or mold releasing agent, which also lowers color reproducibility and transparency in some cases.

In the case where the amount of the phosphonic acid based sequestering agent existing exceeds a definite level, on the other hand, it is sometimes observed that the surface resistivity is lowered, which affects fogging in a non-image area and so on, though there arises no serious problem in a short time use.

The ratio A of the intensity of phosphorus element to the total intensity of all elements detected in the toner by the fluorescent X-ray analysis indicates the amount of phosphorus element on the surface of the electrostatic-image-developing toner. As discussed above, it is preferable that the phosphorus element originates in the phosphonic acid based sequestering agent.

It is preferable that the ratio A is 0.05 or more but not more than 0.5, more preferably 0.07 or more but not more than 0.45 and still more preferably 0.09 or more but not more than 0.40.

The fluorescent X-ray analysis is conducted in vacuo (degree of vacuum: 10 to 100 Pa, using a mixture Ar+$CH_4$ as a PR gas), at an accelerating voltage of 40 kV and at an electrical current value of 70 mV for a measurement time of 15 minutes. The ratio of the intensity of phosphorus element to the total intensity of all elements detected is calculated. The fluorescent X-ray analysis can be conducted using a fluorescent X-ray analyzer XRF1500 (produced by Shimadzu Corp.).

The fluorescent X-ray analysis is conducted by using the toner mother particles (toner particles from which external additives have been removed or those before adding them).

Next, "the toner having been dispersed in an alcoholic solvent followed by drying" will be described in detail.

The alcoholic solvent means a publicly known alcoholic solvent such as methanol, ethanol or isopropanol. It is mixed with ion-exchanged water at a mixing ratio by weight of 20/80 to 80/20 and then 10 to 50% by weight of toner particles are dispersed therein followed by solid/liquid separation and drying.

The ratio B of the intensity of phosphorus element to the total intensity of all elements detected in the toner having been dispersed in the alcoholic solvent followed by drying, by the fluorescent X-ray analysis indicates the intensity ratio of phosphorus element within the electrostatic-image-developing toner of the exemplary embodiment. By dispersing in the alcoholic solvent, the toner particle surface is eluted into the solvent. Thus, it becomes possible to measure the intensity ratio of the inside phosphorus element.

Thus, the ration B is usable as an indication of the amount of the phosphonic acid based sequestering agent existing within the toner particles.

In this exemplary embodiment, it is preferable to control B/A within a specific range so as to improve the dispersibility of the mold releasing agent and/or the coloring agent in the toner.

The B/A ratio is preferably 0.40 or more but not more than 0.75, more preferably 0.45 or more but not more than 0.70 and still more preferably 0.50 or more but not more than 0.65.

<Average Circularity>

It is preferable that the average circularity of the electrostatic-image-developing toner in this exemplary embodiment determined with the use of a flow-type particle image analyzer (FPIA) is about 0.950 or more but not more than about 0.980. It is more preferable that the average circularity is about 0.955 or more but not more than about 0.975 and still more preferably about 0.957 or more but not more than about 0.970.

It is preferable that the average circularity is 0.950 or more, since the toner are not irregular in shape and show excellent transfer properties, durability and fluidity in this case. It is also preferable that the average circularity is not more than 0.980, since spherical particles exist at an appropriate ratio (not too much) and favorable cleaning performance can be established in this case.

In the case of a toner containing a crystalline resin, when the average circularity falls in the more spherical side than the range as defined above (i.e., the average circularity being closer to 1), it is sometimes observed that spherical toner particles containing a large amount of the crystalline resin increases, which results in filming caused by the accumulation at the contact area with a cleaning member, deterioration in the members caused by an increase in torque and filming onto the photoreceptor. When the average circularity is in the more irregular shape side (i.e., the average circularity being closer to 0), cracking occurs in the toner in a development machine. In this case, it is sometimes observed that the crystalline resin is exposed to the cracked interface and thus the charging characteristics, etc. are deteriorated.

The average circularity of the toner can be measured by using a flow-type particle image analyzer FPIA-2000 (manufactured by To a Medical Electronics Co., Ltd.). More specifically speaking, the measurement is conducted by adding 0.1 to 0.5 ml of a surfactant (for example, an alkylbenzenesulfonate) to 100 to 150 ml of water from which solid impurities have been preliminarily removed and then about 0.1 to about 0.5 g of a test sample is added.

The suspension having the test sample dispersed therein is subjected to an ultrasonic dispersion treatment by using an ultrasonic dispersion machine for 1 to 3 minutes to give a dispersion concentration of 3,000 to 10,000 particles/μl. Next, the average circularity of the toner is measured with the apparatus as described above.

It is also preferable that the number ratio of particles having circularity of 0.970 or less within the particle diameter range of 0.5 times or more but not more than 0.7 times larger than the number-average particle diameter is about 1.5% or more but not more than about 15.5%.

It is preferable that the number ratio of particles having circularity of 0.970 or less within the particle diameter range of 0.5 times or more but not more than 0.7 times larger than the number-average particle diameter falls within the range as specified above. This is because there are few small-sized or spherical toner particles in this case and thus excellent cleaning properties and transfer properties can be obtained. This is furthermore preferable, since only a small amount of an external additive is required for improving the performance-holding properties, which makes it possible to prevent the photoreceptor from contamination with the released additive or contamination within the machine.

The range as specified above is more preferably about 2.5% or more but not more than about 13.5% and still more preferably about 3.5% or more but not more than about 12.5%.

<D50v, GSDv and GSDp>

It is preferable that the volume-average particle diameter D50v of the toner in the present exemplary embodiment is 3 μm or more but not more than 7 μm, more preferably 5 μm or more but not more than 6.5 μm. It is preferable that the volume-average particle diameter D50v of the toner is 3 μm or more, since the toner shows good charging properties, scattering of the toner to the environment can be prevented and fog on can be prevented. It is also preferable that the volume-average particle diameter D50v is not more than 7 μm, since a high image resolution can be obtained and thus high image qualities can be established.

It is preferable that the volume average particle diameter distribution GSDv of the toner is 1.28 or less. It is preferable that GSDv is 1.28 or less, since a high image clearness and resolution can be obtained. On the other hand, it is preferable that the number-average particle diameter distribution index GSDp is 1.30 or less. It is preferable that the number-average particle diameter distribution index GSDp is 1.30 or less, since a good performance at the early stage and a high reliability can be obtained.

As having been known hitherto, it is difficult to electrostatically control a small-sized toner due to the large adhesion force thereof. In the case of using a two-component developer, such a toner is liable to remain on the carrier. When a mechanical force is loaded repeatedly, it is sometimes observed in such a case that the carrier is contaminated and, in its turn, the deterioration thereof is accelerated.

In the transfer step, in particular, small-sized components of the toner developed on the latent image holding member can be hardly transferred, which sometimes results in a decrease in the transfer efficiency, an increase in the waste toner, image defects or the like. When these problems arise, an electrostatically non-controlled toner and a reversely charged toner, which cause the contamination of the environment, increase. Among all, these non-controlled toners are accumulated on the charged roll, which sometimes results in charge failures.

Moreover, there is a tendency that the small-sized toner is not sufficiently incorporated into a crystalline resin, which sometimes results in filming or the like. On the other hand, a toner having a large-sized component sometimes undergoes cracking in the development machine or blows out from the development machine, thereby causing deterioration in image qualities due to charge failures.

It is preferable that the volume average particle diameter distribution GSDv and the number-average particle diameter distribution index GSDp respectively fall within the ranges as specified above, since the problems as discussed above scarcely arise.

It is more preferable that the volume average particle diameter distribution GSDv is 1.25 or less and the number-average particle diameter distribution index GSDp is 1.25 or less.

The volume-average particle diameter D50v and various particle diameter distribution indexes can be measured by using a Multisizer II (manufactured by Beckman Coulter, Inc.) and an electrolyte ISOTON-II (manufactured by Beckman Coulter, Inc.).

In the measurement, 0.5 mg or more but not more than 50 mg of a sample to be measured is added to 2 ml of a 5% by weight aqueous solution of a surfactant such as a sodium alkylbenzenesulfonate solution employed as a dispersing agent. Next, it is added to 100 ml to 150 ml of an electrolyte.

The electrolyte having the sample dispersed therein is dispersed in a dispersion machine for 1 minute. Next, the particle diameter distribution of the particles having diameters of 2 μm or more but not more than 50 μm is measured by using the Multisizer II as described above with the use of a 100 μm aperture as the aperture diameter. 50,000 particles are sampled.

Based on the particle diameter distribution thus determined, cumulative distributions by volume and by number are drawn, from the side of the smallest diameter, on the basis of separated particle diameter ranges (channels). The particle diameter when the cumulative percentage becomes 16% is defined as the cumulative volume-average particle diameter D16v and as the cumulative number-average particle diameter D16p, while the particle diameter when the cumulative percentage becomes 50% is defined as the cumulative volume-average particle diameter D50v and as the cumulative number-average particle diameter D50p. Further, the particle diameter when the cumulative percentage becomes 84% is defined as the cumulative volume-average particle diameter D84v and as the cumulative number-average particle diameter D84p.

The volume-average particle diameter distribution index (GSDv) is defined as $(D84v/D16v)^{1/2}$, while the number average particle diameter distribution index (GSDp) is defined as $(D84p/D16p)^{1/2}$.

<Glass Transition Temperature>

Although the glass transition temperature Tg of the toner of the present exemplary embodiment is not particularly restricted, a range thereof of 45° C. or higher but not higher than 60° C. is preferably selected. It is preferable that the glass transition temperature is 45° C. or higher, since a favorable toner storability, a favorable fixed image storability and a high durability in an actual machine can be established. It is also preferable that the glass transition temperature is not higher than 60° C., since the fixation temperature does not become too high and an excessively high temperature is not required in the particularization step.

Tg is measured in accordance with ASTMD3418-8 by using a DSC measurement apparatus (a differential scanning calorimeter DSC60A manufactured by Shimadzu Corporation). The melting temperatures of indium and zinc are used in temperature correction in a detection part of the apparatus, and the heat of fusion of indium is used in correction of heat quantity. With an empty pan set for comparison, a sample is placed on an aluminum pan and measured at a temperature elevating speed of 10° C./min.

<Charge Amount>

It is preferable that the charge amount of the electrostatic-image-developing toner of the exemplary embodiment, expressed in the absolute value, is 10 µC/g or more but not more than 40 µC/g, more preferably 15 µC/g or more but not more than 35 µC/g. It is preferable that the charge amount is 10 µC/g or more, since no stain arises in the background. It is also preferable that the charge amount is not more than 40 µC/g, since a favorable image density can be obtained.

It is preferable that the ratio of the charge amount of the electrostatic-image-developing toner in summer (28° C. 85% RH) RH to that in winder (10° C., 30% RH) is 0.5 or more but not more than 1.5, more preferably 0.7 or more but not more than 1.3. From the practical standpoint, it is preferable that the ratio falls within this range, since the toner shows a low environment-dependency and stable charging properties.

Next, other components constituting the electrostatic-image-developing toner of the present exemplary embodiment will be illustrated.

The electrostatic-image-developing toner of the exemplary embodiment contains a binder resin preferably together with a mold releasing agent and/or a coloring agent. It is more preferable that the toner contains a binder resin, a mold releasing agent and a coloring agent.

<Binder Resin>

In the toner of the exemplary embodiment, it is preferable to use a crystalline resin as the binder resin. It is particularly preferable to use a non-crystalline resin together, if necessary.

In this exemplary embodiment, the term "crystalline resin" means a resin having a clear endothermic peak in measurement (i.e., a peak having a half width of the endothermic peak of 15° C. or less) in differential scanning calorimetry (DSC), while the term "non-crystalline resin" means a resin not having such a clear peak as described above.

Regardless of whether a crystalline resin or a non-crystalline resin, the weight-average molecular weight of the binder resin is preferably 10,000 or more, more preferably 15,000 or more but not more than 500,000.

As the crystalline resin, use can be made of, for example, a polyester resin, a crystalline vinyl-based resin and so on. As the non-crystalline resin, use can be made of a polyester resin, a polyurethane resin, an epoxy resin, a polyol resin and so on. Next, the binder resins to be used in the invention will be illustrated separately divided in crystalline resins and non-crystalline resins.

[Crystalline Resin]

The content of the crystalline resin in the toner mother particles is preferably 2% by weight or more but not more than 30% by weight, more preferably 3% by weight or more but not more than 15% by weight. It is preferable that the content of the crystalline resin is 2% by weight or more, since good fixability in the low temperature range can be obtained. Also, it is preferable that the content of the crystalline resin is not more than 30% by weight, since uneven gloss and filming can be prevented during fixation in the medium or high temperature range.

The melting temperature of the crystalline resin is preferably 45° C. or higher but not higher than 110° C., more preferably 50° C. or higher but not higher than 100° C., more preferably 55° C. or higher but not higher than 90° C.

It is preferable that the melting temperature of the crystalline resin is 45° C. or higher, since the toner shows an excellent storability. It is also preferable that the melting temperature of the crystalline resin is not higher than 110° C., since the toner shows good fixability in the low temperature range (hereinafter sometimes called "low-temperature fixability").

The melting temperature of the crystalline resin means one determined by the method according to ASTMD3418-8.

The number-average molecular weight (Mn) of the crystalline resin is preferably 5,000 or more, more preferably 7,000 or more.

It is preferable that the number-average molecular weight (Mn) is 5,000 or more, since the toner may penetrate into the surface of a recording material (a recording medium) such as paper, thus preventing uneven fixation or imparting a high bending resistance to a fixed image.

As described above, use can be made of a crystalline polyester resin, a crystalline vinyl resin etc. as the crystalline resin. It is preferable to use a crystalline polyester resin from the viewpoints of the adhesiveness to paper in the fixation step, charging properties and easiness in regulating the melting temperature in the preferable range. An aliphatic crystalline polyester resin is more preferable since a resin of having a suitable melting temperature can be easily obtained therefrom.

Specific examples of the crystalline vinyl-based resin include vinyl-based resins using long-chain alkyl or alkenyl (meth)acrylates such as amyl(meth)acrylate, hexyl(meth)acrylate, heptyl(meth)acrylate, octyl(meth)acrylate, nonyl(meth)acrylate, decyl(meth)acrylate, undecyl(meth)acrylate, tridecyl(meth)acrylate, myristyl(meth)acrylate, cetyl(meth)acrylate, stearyl(meth)acrylate, oleyl(meth)acrylate and behenyl(meth)acrylate. In the present specification, the term "(meth)acryl" refers to both "acryl" and "methacryl".

As the crystalline polyester rein, on the other hand, use can be made of one that is synthesized from a polycarboxylic acid (preferably a dicarboxylic acid) component and a polyol (preferably a diol) component.

Next, the polycarboxylic acid component and the polyol component will be described in greater detail. In the present specification, the term "crystalline polyester resin" also includes a copolymer produced by copolymerizing a crystalline polyester resin with another component in an amount of 50% by weight or less based on the main chain of the crystalline polyester resin.

The polycarboxylic acid component as described above is preferably an aliphatic dicarboxylic acid and particularly preferably a linear carboxylic acid. Examples thereof include oxalic acid, malonic acid, succinic acid, glutaric acid, adipic acid, pimelic acid, suberic acid, azelaic acid, sebacic acid, 1,9-nonanedicarboxylic acid, 1,10-decanedicarboxylic acid, 1,11-undecanedicarboxylic acid, 1,12-dodecanedicarboxylic acid, 1,13-tridecanedicarboxylic acid, 1,14-tetradecanedicarboxylic acid, 1,16-hexadecanedicarboxylic acid and 1,18-octadecanedicarboxylic acid, and lower alkyl esters and acid anhydrides thereof, though the exemplary embodiment is not restricted thereto.

In addition to the aliphatic dicarboxylic acid component as cited above, it is preferable that the polycarboxylic acid component includes components such as a dicarboxylic acid component having a double bond and a dicarboxylic acid component having a sulfonate group. The dicarboxylic acid component having a double bond includes not only components derived from dicarboxylic acids having double bonds but also components derived from lower alkyl esters or acid anhydrides of dicarboxylic acids having double bonds. The dicarboxylic acid component having a sulfonate group includes not only components derived from dicarboxylic acids having sulfonate groups but also components derived from lower alkyl esters or acid anhydrides of dicarboxylic acids having sulfonate groups.

The dicarboxylic acid having a double bond can be appropriately used in crosslinking the entire resin by utilizing the double bonds therein for preventing hot offset upon fixation. Examples of the dicarboxylic acid include fumaric acid, maleic acid, 3-hexenedioic acid and 3-octenedioic acid, and lower alkyl esters and acid anhydrides thereof, though the exemplary embodiment is not restricted thereto. Among them, fumaric acid, maleic acid etc. are preferable from the viewpoint of cost.

The dicarboxylic acid having a sulfonate group is effective in improving dispersion of a coloring agent such as a pigment or the like. In the step of emulsifying or suspending the entire resin in water to form particles, the sulfonate group enables the emulsification or suspension of the resin with the use of no or only a small amount a surfactant.

Examples of the dicarboxylic acid having a sulfonate group include sodium 2-sulfoterephthalate, sodium 5-sulfoisophthalate and sodium sulfosuccinate, though the exemplary embodiment is not restricted thereto. It is also possible to employ lower alkyl esters and acid anhydrides thereof. Among them, sodium 5-sulfoisophthalate or the like is preferable from the viewpoint of cost.

The content of the polycarboxylic acid component (the dicarboxylic acid component having a double bond and/or the dicarboxylic acid component having a sulfonate group) other than the aliphatic dicarboxylic acid component in the polycarboxylic acid component is preferably 1% by constitutional mole or more but not more than 20% by constitutional mole, more preferably 2% by constitutional mole or more but not more than 10% by constitutional mole.

It is preferable that the content as described above is 1% by constitutional mole or more, since, when a pigment is employed as a coloring agent, the pigment shows a high dispersibility in the toner mother particles. It is also preferable that, in the case where the toner is prepared by the aggregation/coalescence method, an appropriate diameter of the emulsified particle in the dispersion can be obtained and the toner diameter by aggregation can be controlled. On the other hand, it is preferable that the content is not more than 20% by constitutional mole, since a good crystallinity of the crystalline polyester resin is obtained, the melting temperature would not decrease, and a good storability of an image can be established. It is also preferable that, in the case where the toner is prepared by the aggregation/coalescence method, the diameter of the emulsified particle in the dispersion is maintained at an appropriate level to form latex without being dissolved in water.

In the present exemplary embodiment, the term "% by constitutional mole" means the proportion where the amount of each component (the polycarboxylic acid component or the polyol component) in the polyester resin is referred to as 1 unit (mol).

On the other hand, the polyol component is preferably an aliphatic diol, and examples thereof include ethylene glycol, 1,3-propane diol, 1,4-butane diol, 1,5-pentane diol, 1,6-hexane diol, 1,7-heptane diol, 1,8-octane diol, 1,9-nonane diol, 1,10-decane diol, 1,11-undecane diol, 1,12-dodecane diol, 1,13-tridecane diol, 1,14-tetradecane diol, 1,18-octadecanediol and 1,20-eicosane diol and the like, though the exemplary embodiment is not restricted thereto.

It is preferable that the polyol component contains 80% by constitutional mole or more of an aliphatic diol component optionally together with other required component. It is more preferable that the polyol component contains 90% by constitutional mole or more of the aliphatic diol component.

It is preferable that the content is 80% by constitutional mole or more, since the polyester resin shows a favorable crystallinity, an appropriately maintained melting temperature, a high toner blocking resistance, a good image storability, and a good low-temperature fixability.

On the other hand, examples of the other components contained if necessary include components such as a diol component having a double bond and a diol component having a sulfonate group.

Examples of the diol component having a double bond include 2-butene-1,4-diol, 3-butene-1,6-diol, 4-butene-1,8-diol, etc. On the other hand, examples of the diol component having a sulfonate group include sodium benzene 1,4-dihydroxy-2-sulfonate, sodium benzene 1,3-dihydroxymethyl-5-sulfonate, 2-sulfo-1,4-butanediol sodium salt, etc.

In the case of adding such a polyol component (the diol component having a double bond and/or the diol component having a sulfonate group) other than the linear aliphatic diol component, the content thereof in the polyol components is preferably 1% by constitutional mole or more but not more than 20% by constitutional mole, more preferably 2% by constitutional mole or more but not more than 10% by constitutional mole.

It is preferable that the content is 1% by constitutional mole or more, since the pigment is well dispersed and the diameter of the emulsified particle is not too large, thereby facilitating the regulation of the toner diameter by aggregation. On the other hand, it is also preferable that the content is not more than 20% by constitutional mole, since the crystallinity of the polyester resin is maintained at an appropriate level, the melting temperature is not too low and a favorable image storability is obtained. Moreover, it is possible to avoid the occurrence of problems of, e.g., the diameter of the emulsified particle is so small that the toner would hardly aggregate.

The method of producing the crystalline polyester resin is not particularly limited. That is, the resin can be produced by a commonly employed method of polymerizing a polyester by reacting a polycarboxylic acid component with a polyol component. An appropriate method may be selected from among, for example, the direct polycondensation method, the ester exchange method and so on depending on the monomer types. The molar ratio of the polycarboxylic acid component to the polyol component (polycarboxylic acid component/polyol component) to be reacted with each other cannot be generalized because of varying depending on reaction conditions etc. In usual, the ratio is about 1/1.

It is preferable to produce the crystalline polyester resin at a polymerization temperature of 180° C. or higher but not higher than 230° C. If necessary, the reaction is carried out in an evacuated reaction system while removing water and alcohol generated in the course of the condensation. When the monomers are not dissolved or compatible with each other at the reaction temperature, a high-boiling solvent may be added as a solubilization aid to thereby dissolve the monomers. It is preferable to carry out the polycondensation while distilling off the solubilization aid. When there is a monomer showing a poor compatibility in the copolymerization, it is advantageous that the poorly compatible monomer is previously condensed with the polycarboxylic acid component or polyol component to be polycondensed followed by the copolymerization with the major component.

As a catalyst usable in the production of the crystalline polyester resin, there can be enumerated alkali metal compounds such as sodium, lithium etc.; alkaline earth metal compounds such as magnesium, calcium etc.; metal compounds such as zinc, manganese, antimony, titanium, tin, zirconium, germanium etc.; and phosphoric acids, phosphorous acids, amine compounds, and the like. Specific examples thereof are as follows.

Namely, examples of the catalyst include sodium acetate, sodium carbonate, lithium acetate, calcium acetate, zinc stearate, zinc naphthenate, zinc chloride, zinc acetate, manganese acetate, manganese naphthenate, titanium tetraethoxide, titanium tetrapropoxide, titanium tetraisopropoxide, titanium tetrabutoxide, antimony trioxide, triphenyl antimony, tributyl antimony, tin formate, tin acetate, tin oxalate tetraphenyl tin, dibutyltin dichloride, dibutyltin oxide, diphenyltin oxide, tin disulfide, zirconium tetrabutoxide, zirconium naphthenate, zirconyl carbonate, zirconyl acetate, zirconyl stearate, zirconyl octylate, germanium oxide (germanium dioxide), triphenyl phosphite, tris(2,4-di-t-butylphenyl)phosphite, ethyltriphenyl phosphonium bromide, triethylamine, triphenylamine and so on.

From the viewpoint of facilitating the achievement of both of a high low-temperature fixability and an excellent effect of preventing uneven gloss, dibutyltin oxide is preferable among the catalysts cited above.

To regulate the melting temperature, molecular weight etc. of the crystalline resin, use can be made of compounds having a shorter-chain alkyl or alkenyl group, an aromatic ring, etc. in addition to the polymerizable monomers described above.

Specific examples of such compounds include, for the dicarboxylic acid, alkyl dicarboxylic acids such as succinic acid, malonic acid and oxalic acid, aromatic dicarboxylic acids such as phthalic acid, isophthalic acid, terephthalic acid, homophthalic acid, 4,4'-bibenzoic acid, 2,6-naphthalene dicarboxylic acid and 1,4-naphthalene dicarboxylic acid, and nitrogen-containing aromatic dicarboxylic acids such as dipicolinic acid, dinicotinic acid, quinolinic acid and 2,3-pyrazine dicarboxylic acid; for the diols, short-alkyl diols such as ethanediol, propylene glycol and butanediol; and for the vinyl polymerizable monomers having a short-chain alkyl group, short-chain alkyl or alkenyl(meth)acrylates such as methyl (meth)acrylate, ethyl(meth)acrylate, propyl(meth)acrylate and butyl(meth)acrylate, vinyl nitrites such as acrylonitrile and methacrylonitrile, vinyl ethers such as vinyl methyl ether and vinyl isobutyl ether, vinyl methyl ketone, vinyl ethyl ketone and vinyl isopropenyl ketone, and olefins such as ethylene, propylene, butadiene and isoprene. Either one of these polymerizable monomers or a combination of two or more thereof may be used.

[Non-crystalline Resin]

In the toner of the present exemplary embodiment, a non-crystalline resin may be used as the binder resin together with the crystalline resin.

Although the molecular weight of the non-crystalline resin usable herein is not particularly restricted, it is preferable, in the case of producing the toner by using the aggregation/coalescence method as will be described hereinafter, that a non-crystalline resin having a high weight-average molecular weight (Mw) (a high-molecular weight component) together with another non-crystalline resin having a low weight-average molecular weight (a low-molecular weight component).

In this case, it is preferable that the Mw of the high-molecular weight component is 50,000 or more but not more than 300,000, more preferably 50,000 or more but not more than 200,000 and particularly preferably 55,000 or more but not more than 150,000. It is preferable to control the Mw of the high-molecular weight component within the range as defined above, since it becomes more effectively compatible with the crystalline resin and, once compatibilized, the separation from the crystalline resin can be prevented.

On the other hand, it is preferable that the Mw of the low-molecular weight component is 8,000 or more but not more than 50,000, more preferably 8,000 or more but not more than 45,000 and particularly preferably 9,000 or more but not more than 40,000.

It is preferable to control the Mw of the low-molecular weight component within the range as defined above, since the high-molecular weight component can be well enclosed in the toner mother particles in the step of heating and fusing aggregated particles consisting of the starting materials in the aggregation/coalescence method so that the exposure of the crystalline resin on the toner mother particles can be prevented.

In the case of using a mixture of the high-molecular weight component with the low-molecular weight component as described above, the mixing ratio thereof (high-molecular weight component/low-molecular weight component) preferably ranges from 35/65 to 95/5, more preferably from 40/60 to 90/10 and still more preferably from 50/50 to 85/15.

It is preferable that the high-molecular weight component includes an alkenylsuccinic acid or its anhydride with trimellitic acid or its anhydride as the constituting monomers thereof. Because of having a highly hydrophobic alkenyl group, the alkenylsuccinic acid or its anhydride is easily compatible with the crystalline polyester resin.

The molecular weight is determined by using an HLC-8120GPC, SC-8020 apparatus (manufactured by TOSOH CORPORATION), two TSK gel, Super HM-H columns (6.0 mm i.d.×15 cm), and THF (tetrahydrofuran) as an eluent. The measurement conditions are as follows: sample concentration: 0.5%; flow rate: 0.6 ml/min; sample injection amount: 10 µl; measuring temperature: 40° C.; and calibration curve: prepared from 10 samples including A-500, F-1, F-10, F-80, F-380, A-2500, F-4, F-40, F-128, and F-700. In analyzing the samples, data are collected at intervals of 300 ms.

Examples of the alkenylsuccinic acid component include n-dodecenylsuccinic acid, isododecenylsuccinic acid, n-octenylsuccinic acid, n-octadecenylsuccinic acid and acid anhydrides, acid chlorides and lower alkyl (having 1 to 3 carbon atoms) esters thereof.

In the case of carrying a polyvalent (trivalent or higher) carboxylic acid, a polymer chain can have a crosslinked structure. It is preferable to have such a crosslinked structure, since an effect of fixing a compatibilized crystalline polyester resin and preventing it from separation can be thus established. Examples of the trivalent or higher carboxylic acid include hemimellitic acid, trimellitic acid, trimesic acid, mellophanic acid, prehnitic acid, pyromellitic acid, mellitic acid, 1,2,3,4-butane tetracarboxylic acid and acid anhydrides, acid chlorides and lower alkyl (having 1 to 3 carbon atoms) esters thereof.

The method of producing the non-crystalline polyester resin is not particularly limited. That is, the resin can be produced by a commonly employed method of polymerizing a polyester. As the carboxylic acid component to be used in the synthesis of the non-crystalline polyester resin, use can be made of the various dicarboxylic acids cited above with respect to the crystalline polyester resin. As the alcohol component, use can be also made of the various diols usable in synthesizing non-crystalline polyester resins. In addition to the aliphatic diols cited above with respect to the crystalline polyester resin, it is possible to use, for example, bisphenol A, bisphenol A/ethylene oxide adduct, bisphenol A/propylene oxide adduct, hydrogenated bisphenol A, bisphenol S, bisphenol S/ethylene oxide adduct, bisphenol S/propylene oxide adduct, etc. From the viewpoints of toner productivity, heat resistance and transparency, bisphenol S and bisphenol S derivatives such as bisphenol S/ethylene oxide adduct and bisphenol S/propylene oxide adduct are particularly preferably used. Both of the carboxylic acid component and alcohol component may contain plural components, and in particular, bisphenol S has an effect of improving heat resistance.

[Cross-linking Treatment of Binder Resin and So on]

Next, a crosslinking treatment of the crystalline resin used as the binder resin and the non-crystalline resin used if necessary, and copolymerizable components usable in synthesis of the binder resin will be described in detail.

For the synthesis of the binder resin, other components can be copolymerized, and a compound having a hydrophilic polar group can be used as the copolymerizable component.

Specific examples thereof include dicarboxylic acid compounds having an aromatic ring substituted directly with a sulfonyl group, such as sodium sulfonyl-terephthalate and sodium 3-sulfonyl isophthalate.

In the case where the binder resin is a vinyl-based resin, specific examples of other components include unsaturated aliphatic carboxylic acids such as (meth)acrylic acid and itaconic acid; esters of (meth)acrylic acids and alcohols such as glycerin mono(meth)acrylate, fatty acid-modified glycidyl (meth)acrylate, zinc mono(meth)acrylate, zinc di(meth)acrylate, 2-hydroxyethyl(meth)acrylate, polyethylene glycol (meth)acrylate and polypropylene glycol(meth)acrylate; styrene derivatives having a sulfonyl group in the ortho-, meta- or para-position; and sulfonyl group-substituted aromatic vinyl compounds such as sulfonyl group-containing vinyl naphthalene and the like.

Further, a crosslinking agent can be added if necessary to the binder resin for the purpose of preventing uneven gloss, uneven coloration and hot offset, upon fixation in a high-temperature range.

Specific examples of the crosslinking agent include aromatic polyvinyl compounds such as divinyl benzene and divinyl naphthalene; polyvinyl esters of aromatic polyvalent carboxylic acids such as divinyl phthalate, divinyl isophthalate, divinyl terephthalate, divinyl homophthalate, divinyl/trivinyl trimesate, divinyl naphthalene dicarboxylate and divinyl biphenyl carboxylate; divinyl esters of nitrogen-containing aromatic compounds such as divinyl pyridine dicarboxylate; unsaturated heterocyclic compounds such as pyrrole and thiophene; vinyl esters of unsaturated heterocyclic carboxylic acids such as vinyl pyromucate, vinyl furan carboxylate, vinyl pyrrole-2-carboxylate and vinyl thiophene carboxylate; (meth)acrylates of linear polyvalent alcohols such as butanediol methacrylate, hexanediol acrylate, octanediol methacrylate, decanediol acrylate and dodecanediol methacrylate; branched and substituted polyvalent alcohol (meth)acrylates such as neopentyl glycol dimethacrylate and 2-hydroxy-1,3-diacryloxy propane; and polyvalent polyvinyl carboxylates such as polyethylene glycol di(meth)acrylate, polypropylene polyethylene glycol di(meth)acrylates, divinyl succinate, divinyl fumarate, vinyl/divinyl maleate, divinyl diglycolate, vinyl/divinyl itaconate, divinyl acetone dicarboxylate, divinyl glutarate, divinyl 3,3r-thiodipropionate, divinyl/trivinyl trans-aconate, divinyl adipate, divinyl pimelate, divinyl suberate, divinyl azelate, divinyl sebacate, dodecane diacid divinyl, divinyl brassylate etc.

Particularly in the crystalline polyester resin, an unsaturated polycarboxylic acid such as fumaric acid, maleic acid, itaconic acid or trans-aconic acid may be copolymerized with polyester, and then multiple bonds in the resin may be crosslinked with one another or another vinyl compound. Either one of these crosslinking agents or a combination of two or more thereof may be used.

With respect to the method of crosslinking by the crosslinking agent, use may be made of a method wherein the polymerizable monomer is polymerized together with the crosslinking agent and thus crosslinked or a method wherein, after the binder resin is polymerized while remaining unsaturated portions therein or after the toner is prepared, the unsaturated portions are crosslinked by the crosslinking reaction.

In the case of using a polyester resin as the binder resin, the polymerizable monomer can be polymerized by condensation polymerization. As the catalyst for the condensation polymerization, use can be made of a condensation polymerization catalyst appropriately selected from among those cited above.

In the case of using a vinyl-based resin as the binder resin, the polymerizable monomer can be polymerized by radical polymerization.

Although a radical polymerization initiator may be used without specific limitation, it is preferable to use one allowing emulsion polymerization. Specific examples of the radical polymerization initiator include peroxides such as hydrogen peroxide, acetyl peroxide, cumyl peroxide, tert-butyl peroxide, propionyl peroxide, benzoyl peroxide, chlorobenzoyl peroxide, dichlorobenzoyl peroxide, bromomethyl benzoyl peroxide, lauroyl peroxide, ammonium persulfate, sodium persulfate, potassium persulfate, peroxy carbonate, diisopropyl tetralin hydroperoxide, 1-phenyl-2-methylpropyl-1-hydroperoxide, pertriphenyl acetate-tert-butyl hydroperoxide, tert-butyl performate, tert-butyl peracetate, tert-butyl perbenzoate, tert-butyl perphenylacetate, tert-butyl permethoxyacetate, and tert-butyl perN-(3-toluoyl)carbamate; azo compounds such as 2,2'-azobispropane, 2,2'-dichloro-2,2'-azobispropane, 1,1'-azo(methylethyl)diacetate, 2,2'-azobis(2-amidinopropane)hydrochloride, 2,2'-azobis(2-amidinopropane)nitrate, 2,2'-azobisisobutane, 2,2'-azobisisobutylamide, 2,2'-azobisisobutyronitrile, methyl 2,2'-azobis-2-methylpropionate, 2,2'-dichloro-2,2-azobisbutane, 2,2'-azobis-2-methylbutyronitrile, dimethyl 2,2'-azobisisobutyrate, 1,1'-azobis(sodium 1-methylbutyronitrile-3-sulfonate), 2-(4-methylphenylazo)-2-methylmalonodinitrile, 4,4-azobis-4-cyanovaleric acid, 3,5-dihydroxymethylphenylazo-2-methylmalonodinitrile, 2-(4-bromophenylazo)-2-allylmalonodinitrile, 2,2'-azobis-2-methylvaleronitrile, dimethyl 4,4'-azobis-4-cyanovalerate, 2,2'-azobis-2,4-dimethylvaleronitrile, 1,1'-azobiscyclohexanenitrile, 2,2'-azobis-2-propylbutyronitrile, 1,1'-azobis-1-chlorophenylethane, 1,1'-azobis-1-cyclohexanecarbonitrile, 1,1'-azobis-1-cycloheptanenitrile, 1,1'-azobis-1-phenylethane, 1,1'-azobiscumene, ethyl 4-nitrophenylazobenzylcyanoacetate, phenyl azodiphenyl methane, phenyl azotriphenyl methane, 4-nitrophenyl azotriphenyl methane, 1,1'-azobis-1,2-diphenyl ethane, poly(bisphenol A-4,4'-azobis-4-cyanopentanoate) and poly(tetraethyleneglycol-2,2'-azobisisobutyrate); 1,4-bis(pentaethylene)-2-tetrazene, 1,4-dimethoxycarbonyl-1,4-diphenyl-2-tetrazene and so on. It is also possible to use these polymerization initiators as initiators for the crosslinking reaction.

Although the binder resin has been described by referring mainly to the crystalline polyester resin and non-crystalline polyester resin, use can be also made of, styrene and styrene derivatives such as parachlorostyrene and α-methyl styrene; acrylate monomers such as methyl acrylate, ethyl acrylate, n-propyl acrylate, butyl acrylate, lauryl acrylate and 2-ethylhexyl acrylate; methacrylate monomers such as methyl methacrylate, ethyl methacrylate, n-propyl methacrylate, lauryl methacrylate and 2-ethylhexyl methacrylate; ethylenically unsaturated monomers such as acrylic acid, methacrylic acid and sodium styrenesulfonate; vinyl nitrites such as acrylonitrile and methacrylonitrile; vinyl ethers such as vinyl methyl ether and vinyl isobutyl ether; vinyl ketones such as vinyl methyl ketone, vinyl ethyl ketone and vinyl isopropenyl ketone; homopolymers of olefinic monomers such as ethylene, propylene and butadiene, copolymers including a combination of two or more of these monomers, or mixtures thereof; non-vinyl-based condensed resins such as an epoxy resin, a polyester resin, a polyurethane resin, a polyamide resin, a cellulose resin and a polyether resin, or mixtures thereof with the vinyl-based resin, and graft polymers obtained by polymerizing the vinyl monomers in the presence of these resins.

In the case of producing the toner of this exemplary embodiment by the aggregation/coalescence method as will be described hereinafter, the binder resin is prepared as a resin particle dispersion. This resin particle dispersion can be easily obtained by the emulsion polymerization method of a polymerization method in a non-uniform dispersion system similar thereto. Alternatively, it can be obtained by an arbitrary method such as a method wherein a polymer, which has been uniformly polymerized by the solution polymerization method, the block polymerization method or the like, is added together with a stabilizer to a solvent in which the polymer is insoluble followed by mechanical mixing and dispersion.

In the case of using a vinyl-based monomer, for example, a resin particle dispersion can be prepared by the emulsion polymerization method or the seed polymerization method with the use of an ionic surfactant or the like appropriately together with a nonionic surfactant.

Examples of the surfactant to be used herein include anionic surfactants such as sulfate salt-based surfactants, sulfonate-based surfactants, phosphate-based surfactants and soap type surfactants; cationic surfactants such as amine salt type surfactants and quaternary ammonium salt type surfactants; nonionic surfactants such as polyethylene glycol-based surfactants, alkyl phenol ethylene oxide adduct-based surfactants, alkyl alcohol ethylene oxide adduct-based surfactants and polyhydric alcohol-based surfactants; and various graft polymers, though the exemplary embodiment is not restricted thereto.

In the case of preparing the resin particle dispersion via emulsion polymerization, it is particularly preferable to add a small amount of an unsaturated acid (for example, acrylic acid, methacrylic acid, maleic acid, styrenesulfonic acid, etc.) as a part of the monomer components to form a protective colloidal layer on the particle surface, thereby enabling soap-free polymerization in the absence of a surfactant.

It is preferable that the volume-average particle diameter of the resin particles in the resin particle dispersion is not more than 1 μm, more preferably 0.01 μm or more but not more than 1 μm. It is preferable that the volume-average particle diameter of the resin particles is not more than 1 μm, since the toner obtained finally has a narrow particle size distribution and little free particles are generated, thereby giving an excellent performance and a high reliability.

So long as the average particle diameter of the resin particles falls within the range as defined above, the above-described problems are solved and localization within the toner is reduced. As a result, it is possible to achieve advantages such that a good dispersion can be obtained in the toner and scattering in performance or reliability can be reduced. The average particle diameter of the resin particles can be measured by using, for example, a laser diffraction particle size measuring instrument (SALD2000A, manufactured by Shimadzu Corporation) or the like.

<Mold Releasing Agent>

It is preferable that the electrostatic-image-developing toner of the present exemplary embodiment contains a mold releasing agent.

As the mold releasing agent, use can be made of publicly known mold releasing agents for toners. Examples thereof include low-molecular polyolefins such as polyethylene, polypropylene and polybutene; fatty acid amides such as silicones, oleicacidamide, erucicacidamide, ricinoleicacid amide and stearic acid amide; vegetable waxes such as carnauba wax, rice wax, candelilla wax, haze wax and jojoba oil; animal waxes such as beeswax; mineral or petroleum waxes such as montan wax, ozokerite, ceresin, paraffin wax, microcrystalline wax and Fischer Tropsch wax; and modified products thereof.

In the case of producing the toner by using the aggregation/coalescence method, the mold releasing agent is dispersed together with the ionic surfactant and polymeric electrolytes such as a polymeric acid and a polymeric base in an aqueous medium and then heated to the melting temperature. At the same time, it is finely divided by a homogenizer capable of giving strong shearing force or a pressure discharging dispersing machine, and then used as a mold releasing agent dispersion containing particles of the mold releasing agent having an average particle diameter of 1 μm or less.

These mold releasing agent particles may be added to a solvent mixture together with the other resin particle components either all at once or in several portions.

The amount of the mold releasing agent in the toner mother particles is preferably 0.5% by weight or more but not more than 50% by weight, more preferably 1% by weight or more but not more than 30% by weight and still more preferably 5% by weight or more but not more than 15% by weight. It is preferable that the content is 0.5% by weight or more, since oilless fixation can be conducted. It is also preferable that the content is not more than 50% by weigh, since the mold releasing agent sufficiently leak out the image surface in the fixation and little remains in the image, thereby giving a high image transparency.

The average dispersion diameter of the mold releasing agent dispersed and contained in the toner is 0.3 μm or more but not more than 0.8 μm, more preferably 0.4 μm or more but not more than 0.8 μm.

It is preferable that the average dispersion diameter of the mold releasing agent is 0.3 μm or more, since a sufficient mold releasability can be obtained. In particular, a sufficient releasability can be obtained even at a high process speed. On the other hand, it is preferable that the average dispersion diameter of the mold releasing agent is not more than 0.8 μm, since a lowering in transparency or exposure of the mold releasing agent on the toner surface scarcely occurs even in the case of using an OHP sheet.

The standard derivation of the dispersion diameter of the mold releasing agent is preferably 0.05 or less, more preferably 0.04 or less. It is preferable that the standard derivation of the dispersion diameter of the mold releasing agent is 0.05 or less, since the releasability, the transparency of an OHP sheet in using and the exposure of the mold releasing agent component to the surface of the toner may not be adversely affected.

The average dispersion diameter of the mold releasing agent dispersed and contained in the toner is determined by analyzing a TEM (transmission electron microscope) photograph with an image analyzer (Luzex image analyzer, manufactured by Nireko Co., Ltd.) and calculating the mean dispersion diameter (=(major axis+minor axis)/2) of the mold releasing agent in 100 toner mother particles, and on the basis of the individual dispersion diameters thus obtained, the standard derivation is determined.

<Coloring Agent>

It is preferable that the toner of the present exemplary embodiment contains a coloring agent. However, it is not required to use a coloring agent in the case where it is intended to use the toner of the exemplary embodiment for a special purpose, for example, not forming a color image but printing coding data by adding an infrared absorbing agent or forming a transparent image.

Examples of the coloring agent to be used in the exemplary embodiment include various pigments such as carbon black, chrome yellow, hanza yellow, benzidine yellow, threne yellow, quinoline yellow, permanent orange GTR, pyrazolone orange, vulcan orange, Watchung red, permanent red, brilliant carmine 3B, brilliant carmine 6B, DuPont oil red, pyrazolone red, lithol red, rhodamine B lake, lake red C, rose Bengal, aniline blue, ultramarine blue, chalco oil blue, methylene blue chloride, phthalocyanine blue, phthalocyanine green and malachite green oxalate; various dyes based on acridine, xanthene, azo, benzoquinone, azine, anthraquinone, thioindigo, dioxazine, thiazine, azomethine, indigo, phthalocyanine, aniline black, polymethine, triphenyl methane, diphenyl methane and thiazole; and mixtures of two or more thereof.

In the case where the toner is prepared by the aggregation/coalescence method, such a coloring agent is dispersed in a solvent and used as a coloring agent dispersion. The volume-average particle diameter of the coloring agent particles in the dispersion is preferably 0.5 μm or less, more preferably 0.05 μm or more but not more than 0.3 μm.

It is preferable that the average particle diameter of the coloring agent particles is not more than 0.5 μm, since the particle size distribution of the finally obtained toner for electrostatic image development can be narrowed and little free particles are generated, thereby giving an electrostatic-image-developing toner having an excellent performance and a high reliability. On the other hand, it is preferable that the average particle diameter of the coloring agent particles is 0.05 μm or more, since favorable coloring properties are obtained in the toner and shape regulation is well conducted in the emulsion aggregation method, thereby giving the desired toner shape.

The ratio of the number of coarse particles having a volume-average particle diameter of 0.8 μm or more to the number of the total particles in the coloring agent dispersion is preferably less than 10% by number. A ratio closer to 0% by number is preferred. The presence of such coarse particles sometimes causes deterioration in the stability of the aggregation step wherein aggregated particles are formed in a starting dispersion containing various toner material components such as a coloring agent dispersion. In addition, it is observed in some cases that coarse colored particles are released and the particle-size distribution is broadened. It is therefore preferable that the ratio of the number of coarse particles having a volume-average particle diameter of 0.8 μm or more in the coloring agent dispersion is less than 10% by number.

The ratio of the number of particles having a volume-average particle diameter of 0.05 μm or less in the coloring agent dispersion is preferably 5% by number or less. The presence of such small particles sometimes causes deterioration in regulation of the shape of the toner mother particles in the fusion step wherein the aggregated particles are fused by heating, which makes it impossible in some cases to obtain an electrostatic-image-developing toner having the desired average circularity.

On the other hand, so long as the average particle diameter of the coloring agent particles and the proportions of coarse particles and small particles are in the respective ranges as described above, these problems never arise, the localization of the coloring agent particles in the toner is decreased, and the dispersion thereof in the toner is improved, which results in an advantage of reducing scattering in performance and reliability.

The volume-average particle diameter of the coloring agent particles can be measured by using a laser diffraction particle size measuring instrument (SALD2000A, manufactured by Shimadzu Corporation) or the like. It is preferable to set the amount of the coloring agent added in the range of 1% by weight or more but not more than 20% by weight based on the entire toner particles.

For dispersing the coloring agent in a solvent, use can be made of an arbitrary method, for example, a method using a rotating shearing homogenizer or a ball mill, sand mill or DYNO-mill having media, without specific restriction.

It is also possible to use a coloring agent having been surface-modified with a rosin, a polymer etc. Such a surface-modified coloring agent is advantageous in that it has been sufficiently stabilized in the coloring agent dispersion, and when the coloring agent is dispersed to a desired average particle diameter in the coloring agent dispersion and mixed with the resin particle dispersion or subjected to the aggregation step etc., the coloring agent particles are not aggregated with one another and can be maintained in a well dispersed state. However, a coloring agent subjected to excessive surface modification may become free without aggregation with the resin particles in the aggregation step. Accordingly, the surface modification is to be conducted under appropriately selected optimum conditions.

Examples of the polymer used in the surface treatment of the coloring agent include an acrylonitrile polymer, a methyl methacrylate polymer, etc.

As the conditions for the surface modification, it is generally possible to use the polymerization method of polymerizing a monomer in the presence of the coloring agent (pigment), a phase separation method which includes dispersing the coloring agent (pigment) in a polymer solution and lowering the solubility of the polymer to precipitate it on the surface of the coloring agent (pigment), or the like.

<Other Additives>

When the toner of the present exemplary embodiment is used as a magnetic toner, a magnetic powder is contained therein. Examples of the magnetic powder usable herein include metals such as ferrite, magnetite, reduced iron, cobalt, nickel and manganese, alloys thereof and compounds containing the metals. If necessary, a wide variety of commonly employed charge controlling agents such as quaternary ammonium salts, Nigrosine compounds and triphenyl methane pigments may also be added.

To the toner of the exemplary embodiment, inorganic particles can be internally added if necessary. From the viewpoint of durability, it is preferable that inorganic particles having a median particle diameter of 5 nm or more but not more than 30 nm and inorganic particles having a median particle diameter of 30 nm or more but not more than 100 nm are contained in an amount of 0.5% by weight or more but not more than 10% by weight based on the toner.

It is preferable that these inorganic particles are added in an amount of 0.5% by weight or more, since a sufficient toughness at fusion can be established by the thus added inorganic particles so that the releasability can be improved in, for example, oilless fixation. This is seemingly because worsening in stringiness in the toner can be prevented thereby. On the other hand, it is preferable that these inorganic particles are added in an amount of not more than 10% by weight, since a sufficient toughness and a high fluidity in the step of fusing the toner can be established and an image with favorable gloss can be obtained.

Specific examples of the inorganic particles include silica, hydrophobated silica, titanium oxide, alumina, calcium carbonate, magnesium carbonate, tricalcium phosphate, colloidal silica, cation surface-treated colloidal silica and anion surface-treated colloidal silica. Although these inorganic particles have been previously treated in the presence of an ionic surfactant by using a sonicator or the like, colloidal silica which does not require this dispersion treatment is more preferably used.

<External Additives>

It is also possible to externally add a publicly known external additive to the toner of the present exemplary embodiment. As the external additive, use can be made of inorganic particles such as silica, alumina, titania, calcium carbonate, magnesium carbonate and tricalcium phosphate can be used. For example, inorganic particles such as silica, alumina, titania and calcium carbonate and resin particles made of, for example, a vinyl resin, a polyester or silicone can be used as a flowability auxiliary agent or a cleaning auxiliary agent. The method of adding the external additive is not particularly limited. It is also possible to add the external additive in a dried state onto the surfaces of the toner particles under loading a shearing force.

The inorganic particles appropriately usable as the external additive are particles having a primary particle diameter of about 5 nm to about 2 μm, preferably from about 5 to about 500 nm. If necessary, it is preferable to use two or more kinds of inorganic particles in combination. In particular, an external additive having a median particle diameter of 100 nm or more is useful because of having a weak adhesiveness to the toner surface, showing little change in structure over a prolonged user and contributing to the maintenance of the structure of a small particle size product.

The specific surface area of the inorganic particles determined by the BET method preferably ranges from 20 to 500 $m^2/g$. It is preferable that the proportion of the inorganic particles added to the toner ranges from 0.01 to about 5% by weight, more preferably from 0.01 to 2.0% by weight.

Examples of the inorganic particles include a silica powder, alumina, titanium oxide, barium titanate, magnesium titanate, calcium titanate, strontium titanate, zinc oxide, silica sand, clay, mica, wollastonite, diatomaceous earth, chromium oxide, cerium oxide, red iron oxide, antimony trioxide, magnesium oxide, zirconium oxide, barium sulfate, barium carbonate, calcium carbonate, silicon carbide, silicon nitride and so on. Among these, a silica powder is particularly preferred.

The silica powder as used herein means a powder having an Si—O—Si bond and includes both a silica powder produced by the dry process and a silica powder produced by the wet process. Also, the silica powder may be any of anhydrous silicon dioxide, aluminum silicate, sodium silicate, potassium silicate, magnesium silicate, zinc silicate and the like, but a silica powder containing about 85% by weight or more of $SiO_2$ is preferred.

Although various commercially available silica products may be enumerated as specific examples of the silica powder, those having a hydrophobic group on the surface are preferred and examples thereof include AEROSIL R-972, R-974, R-805 and R-812 (all produced by Aerosil Co.) and Talax 500 (produced by Talco Co.). In addition, use may be made of, for example, a silica powder having been treated with a silane coupling agent, a titanium coupling agent, a silicon oil, a silicon oil having an amine in the side chain and so on.

(Method of Producing Electrostatic-image-developing Toner)

The toner of the present exemplary embodiment can be produced by a publicly known method of producing a toner. From the viewpoints of easiness in controlling the toner properties and easiness in controlling the amount of the phosphonic acid based sequestering agent contained in the toner, it is preferable to produce the toner by a so-called wet production method, i.e., a production method including a particularization step of forming toner mother particles containing at least a binder resin and a mold releasing agent in water, an organic solvent or a mixture of the same (called "an aqueous medium" in general), and a washing/drying step of washing and drying the toner mother particles. By using the dry method whereby the phosphonic acid based sequestering agent can be easily contained in the toner mother particles, the toner of the exemplary embodiment can be easily obtained.

The wet production method includes: (1) the suspension polymerization method wherein a mold releasing agent and other components employed if necessary (for example, a coloring agent) are suspended together with a polymerizable monomer for forming a binder resin (for example, a crystalline resin) and then the polymerizable monomer is polymerized; (2) the solution suspension method wherein toner-constituting materials such as a compound having an ionic leaving group, a binder resin such as a crystalline resin, a mold releasing agent and so on are dissolved in an organic solvent and dispersed in a suspended state in an aqueous solvent followed by the removal of the organic solvent; and (3) the emulsion polymerization method wherein a binder resin component such as a crystalline resin is prepared by emulsion polymerization and then subjected to hetero-aggregation together with a mold releasing agent dispersion and so on followed by fusion, though the exemplary embodiment is not restricted thereto. In addition, citation may be made of: (4) a method wherein a binder resin component such as a crystalline resin, which has been obtained by block polymerization (bulk polymerization), is dispersed together with a surfactant in an aqueous medium under a mechanical shearing force or the like to give a resin particle dispersion and that is then subjected to hetero-aggregation together with a mold releasing agent dispersion and so on followed by fusion.

In the present exemplary embodiment, it is preferable to produce the electrostatic-image-developing toner by the following method, though the exemplary embodiment is not restricted thereto. The method of producing an electrostatic-image-developing toner appropriately usable in the exemplary embodiment is characterized by excluding: (i) a step of dispersing a coloring agent and/or a mold releasing agent in an aqueous medium to give a coloring agent dispersion and/or a mold releasing agent dispersion; (ii) a step of mixing a phosphonic acid based sequestering agent with at least one of the coloring agent dispersion and/or the mold releasing agent dispersion to give a phosphonic acid based sequestering agent mixture dispersion; and (iii) a step of mixing the phosphonic acid based sequestering agent mixture dispersion with a resin particle dispersion and thus aggregating and fusing (coalescing) the dispersions. Hereinafter, the above-described method will be sometimes called the aggregation/coalescence method too. Next, the individual steps will be described in greater detail.

(i) Step of Dispersing Coloring Agent and/or Mold Releasing Agent in an Aqueous Medium to Give Coloring Agent Dispersion and/or Mold Releasing Agent Dispersion In the exemplary embodiment, the term "aqueous medium" means water, an organic solvent or a mixture of the same and examples thereof include water such as distilled water and ion-exchanged water, alcohols such as ethanol and methanol and so on. Among them, ethanol or water is preferable and water such as distilled water or ion-exchanged water is still preferable. Either one of these media or a combination of two or more thereof may be used.

The methods of preparing the coloring agent dispersion and the mold releasing agent dispersion are as described above. For example, a method of dispersing the agent together with a surfactant in an aqueous medium by loading a mechanical shearing force may be cited by way of example.

(ii) Step of Mixing Phosphonic Acid Based Sequestering Agent with at Least One of the Coloring Agent Dispersion and the Mold Releasing Agent Dispersion to Give Phosphonic Acid Based Sequestering Agent Mixture Dispersion With respect to the method of mixing the phosphonic acid based sequestering agent with at least one of the coloring agent dispersion and the mold releasing agent dispersion, it is preferable that the phosphonic acid based sequestering agent is dispersed and/or dissolved in an aqueous medium to give a phosphonic acid based sequestering agent-containing liquid and then it is mixed with the coloring agent dispersion or the mold releasing agent dispersion to thereby blend the phosphonic acid based sequestering agent therewith. It is preferable that the content of the phosphonic acid based sequestering agent in the phosphonic acid based sequestering agent-containing liquid ranges from about 3 to about 25%, more preferably from 5 to 15%. In mixing phosphonic acid based sequestering agent-containing liquid with the coloring agent dispersion or the mold releasing agent dispersion, it is preferable to control the temperature to 25 to 50° C., more preferably 30° C. to 45° C. It is also preferable to mix the phosphonic acid based sequestering agent with the coloring agent dispersion. It is more preferable to mix the phosphonic acid based sequestering agent-containing liquid having the phosphonic acid based sequestering agent content within the range as specified above with the coloring agent dispersion under stirring within the temperature range as specified above.

(iii) Step of Mixing the Phosphonic Acid Based Sequestering Agent Mixture Dispersion with Resin Particle Dispersion and thus Aggregating and Fusing (Coalescing) the Dispersions In the case of employing this aggregation/coalescence method, the toner of the exemplary embodiment can be produced via at least the aggregation step, wherein aggregated particles are formed in the starting dispersion prepared by mixing the resin particle dispersion containing, for example, a non-crystalline resin (or a crystalline resin) dispersed therein, the dispersion containing a mixture of the mold releasing agent and/or the coloring agent with the phosphonic acid based sequestering agent, and the fusion step wherein the aggregated particles are fused and coalesced by heating the starting dispersion having the aggregated particles formed therein to the glass transition temperature of the binder resin (or the melting temperature of the crystalline resin) or higher.

If necessary, the starting dispersion may further contain other dispersions such as an inorganic particle dispersion and a resin particle dispersion containing a non-crystalline resin dispersed therein. In the case of adding a dispersion of surface-hydrophobated inorganic particles, the dispersibilities of the mold releasing agent and the coloring agent within the toner can be controlled.

Next, the aggregation/coalescence method will be illustrated in greater detail.

The aggregation/coalescence method includes at least the aggregation step and the fusion step. In addition, an adhesion step, wherein aggregated particles having a core/shell structure (i.e., resin particles are adhered to the surface of aggregated particles (core particles) having been formed via the aggregation step), may be introduced thereinto.

<Aggregation Step>

In the aggregation step, aggregated particles are formed in a starting dispersion having been prepared by mixing a resin particle dispersion having the particles of a resin (a crystalline resin, etc.) dispersed therein with a mold releasing agent dispersion having the mold releasing agent dispersed therein, a coloring agent dispersion having the coloring agent dispersed therein and other dispersions, if necessary. It is preferable to add the phosphonic acid based sequestering agent to the mold releasing agent dispersion and/or the coloring agent dispersion to give a phosphonic acid based sequestering agent mixture dispersion.

More specifically, the starting dispersion obtained by mixing the respective dispersions is heated to aggregate particles in the starting dispersion, thereby forming aggregated particles. It is preferable that the heating is carried out at within a temperature range lower than the melting temperature of the crystalline resin (lower by 10° C. to 20° C. than the melting temperature).

The aggregated particles are formed by adding an aggregating agent preferably at 20° C. to 30° C. under stirring in a rotating shearing homogenizer and then adjusting the pH value of the starting dispersion to the acidic level.

In the case of producing the electrostatic-image-developing toner by using the aggregation/coalescence method, therefore, it is preferable that the phosphonic acid based sequestering agent is not precipitated under the acidic conditions. Namely, it is preferable to use a phosphonic acid based sequestering agent which is soluble in the aqueous medium (preferably water) under the acidic conditions.

As the aggregating agent to be used in the aggregation step, use can be appropriately made of a surfactant having reverse polarity to that of the surfactant used as a dispersant to be added to the starting dispersion, that is, an inorganic metal salt or a metal complex having a divalent or higher metal element. It is particularly preferable to use a metal complex because the amount of the surfactant used can be reduced and charging properties are improved.

Examples of the inorganic metal salt include metal salts such as calcium chloride, calcium nitrate, barium chloride, magnesium chloride, zinc chloride, aluminum chloride and aluminum sulfate, and inorganic metal salt polymers such as poly(aluminum chloride), poly(aluminum hydroxide) and poly(calcium sulfide). Among these compounds, the aluminum salts and polymers thereof are particularly preferable. To achieve a sharper particle-size distribution, the valence of the inorganic metal salt is more preferably divalent than monovalent, trivalent than divalent, or tetravalent than trivalent, and given the same valence, an inorganic metal salt polymer of polymerization type is more preferable.

It is preferable that the inorganic particle dispersion having the inorganic metal salt is added to the starting dispersion mixture so as to aggregate together. Thus, the aggregating agent can effectively act on the molecular chain ends of the binder resin, thereby contributing to the formation of the crosslinked structure.

The inorganic particle dispersion can be prepared by an arbitrary method with the use of, for example, a ball mill, a sand mill or an ultrasonic dispersion machine of the shearing homogenizer type. It is preferable that the average particle diameter of the inorganic particle dispersion is 100 nm or more but not more than 500 nm.

In the aggregation step, the inorganic particle dispersion can be added either stepwise or continuously. These procedures are effective in uniformly dispersing the metal ion component in the inorganic particle dispersion from the toner surface to the inside thereof. It is particularly preferable that the inorganic particle dispersion is added in three or more steps in the case of adding stepwise, or at a slow speed of about 0.1 g/ml or less in the case of adding continuously.

Although the amount of the inorganic particle dispersion added varies depending on the type of the metal required and the extent of the crosslinked structure formation, it is preferably 0.5 parts by weight or more but not more than 10 parts by weight, more preferably 1 part by weight or more but not more than 5 parts by weight per 100 parts by weight of the binder resin.

In the aggregation step, the amount of a divalent or higher metal element contained in the toner mother particles can be regulated by controlling the type and amount of the inorganic metal salt or the metal complex containing the divalent or higher metal element so long as the formation of the aggregated particles is not affected thereby.

From the viewpoint of more easily achieving the low-temperature fixability and the effect of preventing uneven gloss both at high levels, use can be appropriately made of aluminum sulfate, poly(aluminum chloride) or calcium chloride from among the aggregating agents cited above.

<Adhesion Step>

If necessary, an adhesion step may be carried out after the completion of the aggregation step. In the adhesion step, resin particles are adhered to the surfaces of the aggregated particles having been formed in the aggregation step, thereby forming a coating layer. Thus, a toner having a core/shell structure which consists of the core layer and a shell layer coating the same can be obtained.

The coating layer (shell layer) can be formed usually by further adding a dispersion containing non-crystalline resin particles to the dispersion having aggregated particles (core particles) formed in the aggregation step. In the case of using a non-crystalline resin in addition to the crystalline resin in the aggregation step, the non-crystalline resin used in the adhesion step may be the same as or different from the one used in the aggregation step.

In general, the adhesion step is used in preparing a toner having a so-called core/shell structure which contains the crystalline resin as the binder resin employed as the main component together with the releasing agent. The major object is to prevent the exposure of the releasing agent and crystalline resin contained in the core layer to the toner surface and to compensate for the toughness of the toner particles since the core layer alone has a still insufficient toughness.

In the present exemplary embodiment, it is preferable to additionally add a phosphonic acid based sequestering agent-containing liquid in the step of adding the additional resin particle dispersion to be used as the shell layer or after the addition of the same.

By additionally adding the phosphonic acid based sequestering agent-containing liquid following the formation of the aggregated particles, it is possible to obtain toner mother particles wherein the phosphonic acid based sequestering agent exists in a large amount on the toner surface than in the inside of the toner.

Thus, it becomes possible that, when the ratio of the intensity of phosphorus element to the total intensity of all elements detected in the toner by the fluorescent X-ray analysis is referred to as A and the ratio of the intensity of phosphorus element to the total intensity of all elements detected in the toner, in which toner particles have been dispersed in an alcoholic solvent followed by drying, by the fluorescent X-ray analysis is referred to as B. A and B satisfy the requirement $B/A \leq 1$. The B/A ratio can be regulated within a desired range by controlling the amount and concentration of the phosphonic acid based sequestering agent to be additionally added.

In the exemplary embodiment, B/A preferably ranges from 0.40 to 0.75, more preferably from 0.45 to 0.70 and still more preferably from 0.50 to 0.65. That is, it is preferable to additionally add the phosphonic acid based sequestering agent in an appropriately selected amount to control B/A within the above range.

The intensity ratio represented by A as described above indicates the phosphonic acid based sequestering agent content on the toner surface. It is preferable to regulate A to 0.05 or more but not more than 0.5, more preferably 0.07 or more but not more than 0.45 and still more preferably 0.09 or more but not more than 0.40 by controlling the amount and concentration of the phosphonic acid based sequestering agent to be additionally added.

In the exemplary embodiment, an electrostatic-image-developing toner in which A and B/A are both controlled in the respective desired ranges can be obtained by controlling both of the phosphonic acid based sequestering agent to be added in the aggregation step and the phosphonic acid based sequestering agent to be additionally added.

<Fusion Step>

In the fusion step that is carried out after the completion of the aggregation and adhesion steps, the pH value of the suspension containing the aggregated particles having been formed through these steps is adjusted in the desired range thereby terminating the progress of the aggregation. Next, the suspension is heated to fuse the aggregated particles.

The pH value is adjusted by adding an acid and/or an alkali. Although an arbitrary acid may be used without restriction, it is preferable to use an aqueous solution containing 0.1% by weight or more but not more than 50% by weight of an inorganic acid such as hydrochloric acid, nitric acid or sulfuric acid. Although an arbitrary alkali may be used without restriction too, it is preferable to use an aqueous solution containing 0.1% by weight or more but not more than 50% by weight of an alkali metal hydroxide such as sodium hydroxide or potassium hydroxide.

When a local change in the pH value arises in the course of adjusting the pH value, it is sometimes observed that local breakage of the aggregated particles per se or local excessive aggregation thereof is induced and the shape distribution is worsened. The amount of the acid and/or alkali are to be added increases with an increase in the scale. Since the acid and/or alkali are added from a single site, the acid and alkali concentrations at the addition site are elevated with an increase in the scale.

After adjusting the pH value as described above, the aggregated particles are fused (coalesced) by heating. It is preferable that the aggregated particles are fused by heating to a temperature higher by 10 to 30° C. than the melting temperature of the crystalline resin (or the glass transition temperature of the non-crystalline resin in the case of using the same), i.e., at a temperature higher by 10 to 30° C. than the melting temperature or glass transition temperature of the binder resin.

When heating is carried out for fusion or after the completion of the fusion, crosslinking may be carried out with the use of other components. Crosslinking may be also carried out simultaneously with fusion. In the case of carrying out the crosslinking, use is made of such crosslinking agent and polymerization initiator described above with respect to the production of the toner.

The polymerization initiator may be preliminarily mixed with the starting dispersion in the step of preparing the starting dispersion or may be incorporated into the aggregated particles in the aggregation step. Alternatively, the polymerization initiator may be introduced in the fusion step or after the fusion step. When the polymerization initiator is introduced in the aggregation step, adhesion step or fusion step or after the fusion step, a solution or emulsion of the polymerization initiator can be added to the dispersion. For regulating the degree of polymerization, a publicly known crosslinking agent, chain transfer agent, polymerization inhibitor etc. may be added to the polymerization initiator.

<Washing/drying Step, Etc.>

After the step of fusing the aggregated particles, desired toner particles (toner mother particles) are obtained through an optional washing step, solid/liquid separation step and drying step. Taking the charging properties into consideration, it is preferable that the washing step includes sufficient washing by replacement with ion-exchanged water. The solid/liquid separation step is not specifically limited. From the standpoint of productivity, filtration with suction, filtration under pressure or the like is preferably effected. The drying step is not specifically limited too. From the standpoint of productivity, it is preferable to conduct freeze drying, flash jet drying, fluidized drying, oscillation type fluidized drying or the like. If necessary, various external additives described above can be added to the toner particles (toner mother particles) after drying.

More specifically, to impart fluidity to the toner or to enhance the cleaning properties, the toner may be dried similarly to commonly employed toners and then mixed with an inorganic particles of, for example, silica, alumina, titania or calcium carbonate or resin particles of, for example, a vinyl-based resin, polyester or silicone in dried state while being subject to shearing so that the particles are externally added to the surface of the toner particles.

In the case of adhering these particles to the toner surface in an aqueous medium, use can be made of a dispersion of any of materials commonly usable as external additives for toner surface such as silica, alumina, titania, calcium carbonate, magnesium carbonate or tricalcium phosphate dispersed with the use of an ionic surfactant, a polymer acid or a polymer base.

(Electrostatic Image Developer)

The electrostatic image developer of the present exemplary embodiment (hereinafter, referred to sometimes as merely "developer") contains the toner of the invention, and may be compounded with other components if necessary.

Specifically, in the case of using the toner of the exemplary embodiment alone, it is prepared as a one-component electrostatic image developer. In the case of using the toner in combination with a carrier, it is prepared as a two-component electrostatic image developer. It is preferable to control the toner concentration within a range of 1% by weight or more but not more than 10% by weight.

The carrier is not particularly limited, and carriers publicly known per se can be mentioned. For example, use can be made of publicly known carriers such as carriers having a core material coated with a resin layer (resin-coated carrier) which are described in JP-A-62-39879, JP-A-56-11461 and so on.

Examples of the core material of the resin-coated carrier include shaped products such as an iron powder, ferrite and magnetite, and the average particle diameter thereof is about 30 μm or more but not more than about to 200 μm.

Examples of the coating resin forming the coating layer include styrene and styrene derivatives such as parachlorostyrene and α-methyl styrene; α-methylene fatty monocarboxylic acids such as methyl acrylate, ethyl acrylate, n-propyl acrylate, lauryl acrylate, 2-ethylhexyl acrylate, methyl methacrylate, n-propyl methacrylate, lauryl methacrylate and 2-ethylhexyl methacrylate; nitrogen-containing acryls such as dimethylaminoethyl methacrylate; vinyl nitriles such as acrylonitrile and methacrylonitrile; vinyl pyridines such as 2-vinyl pyridine and 4-vinyl pyridine; vinyl ethers such as vinyl methyl ether and vinyl isobutyl ether; vinyl ketones such as vinyl methyl ketone, vinyl ethyl ketone and vinyl isopropenyl ketone; olefins such as ethylene and propylene; homopolymers of vinyl fluorine-containing monomers such as vinylidene fluoride tetrafluoroethylene and hexafluoroethylene, or copolymers consisting of two or more monomers; silicones such as methyl silicone and methyl phenyl silicone; polyesters containing bisphenol, glycol etc.; epoxy resins; polyurethane resins; polyamide resins; cellulose resins; polyether resins and polycarbonate resins. These resins may be used either alone or as a mixture of two or more thereof.

It is preferable that the amount of the coating resin is 0.1 part by weight or more but not more than 10 parts by weight, more preferably 0.5 parts by weight ore more but not more than 3.0 parts by weight, per 100 parts by weight of the core material. To produce the carrier, a heating kneader, a heating Henschel mixer, an UM mixer etc. can be used. It is also possible to use a heating fluidized rolling bed, a heating kiln etc. depending on the amount of the coating resin. The toner/carrier mixing ratio in the electrostatic image developer can be appropriately selected depending on the purpose without specific restriction.

(Image Forming Method and Image Forming Apparatus)

Now, an image forming method and an image forming apparatus using the electrostatic-image-developing toner and/or the developer of the present exemplary embodiment will be described in detail.

As the image forming method using the toner of exemplary embodiment, use can be made of a publicly known electrophotography method. More specifically, the image forming method is preferably an image forming method including: a latent image forming step of forming an electrostatic latent image on the surface of a latent image holding member; a development step of developing the electrostatic latent image formed on the surface of a latent image holding member with a developer comprising a toner to form a toner image; a transfer step of transferring the toner image formed on the surface of a latent image holding member to the surface of a transfer subject; and a fixation step of fixing the toner image transferred on the surface of the transfer subject; wherein the electrostatic-image-developing toner or the electrostatic image developer of the present exemplary embodiment is employed as the developer. As the transfer subject, a recording material (a recording medium) may be cited by way of example.

In addition to these steps, the image forming method may include publicly known steps usable in the image forming methods by electrophotography, for example, a cleaning step wherein cleaning is conducted while collecting the toner remaining on the surface of the image holding member after the transfer step and a toner reusing step (toner recycling step) wherein the toner having been collected in the cleaning step is reused (recycled) as the developer.

As the image forming apparatus using the toner of exemplary embodiment, use can be made of a publicly known image forming apparatus. More specifically, the image forming apparatus is preferably an image forming apparatus including: a latent image holding member; a charging unit that charges the latent image holding member; an exposing unit that exposes the latent image holding member to light to form an electrostatic latent image on the latent image holding member; a development unit that develops the electrostatic latent image with a developer to form a toner image; and a transfer unit that transfers the toner image on the latent image holding member to a recording material; wherein the electrostatic-image-developing toner or the electrostatic image developer of the exemplary embodiment is employed as the developer.

Similar to the image forming method as described above, the image forming apparatus may include publicly known units usable in the image forming apparatuses by electrophotography, for example, a cleaning unit which conducts cleaning while collecting the toner remaining on the surface of the image holding member after the transfer unit and a toner reusing unit (toner recycling unit) which reuses (recycles) the toner having been collected in the cleaning unit as the developer.

<Latent Image Forming Step>

The latent image forming step is a step of forming an electrostatic latent image by charging the surface of a latent image holding member with a charging unit and then exposing the latent image holding member to light with a laser optical system or an LED array. The charging unit may be any type of charger and examples thereof include non-contact-type chargers such as a corotron and a scorotron and contact-type chargers by which the surface of a latent image holding member is charged by applying voltage to an electroconductive member contacting with the surface of the latent image holding member. However, from the viewpoints of exerting the effects of less ozone generation, high environmental compatibility and excellent printing durability, a charger of the contact charging type is preferable. In the charger of the contact charging type, the electroconductive member is not limited in shape. Namely, use may be made therefor of a brush, a blade, a pin electrode or a roller. The latent image forming method is not particularly limited to the embodiment as described above.

<Development Step>

The development step described above is a step wherein a developer carrier having a developer layer containing at least a toner formed on the surface thereof is contacted with, or made close to, the surface of the latent image holding member thereby allowing toner particles to adhere to an electrostatic latent image on the surface of the latent image holding member, thereby forming a toner image on the surface of the latent image holding member. As the development system, a known system can be used. In the case where the developer is a two-component developer, use may be made of, for example, the cascade system, the magnetic brush system, etc. The development step is not particularly limited to the embodiment as described above.

<Transfer Step>

The transfer step is a step of transferring the toner image formed on the surface of the latent image holding member onto a recording material (a recording medium). In the transfer step, use may be made of either a system of directly transferring a toner image onto a recording material (a recording medium) such as paper or a system of transferring a toner image onto a drum- or belt-shaped intermediate transfer material and then transferring it onto a recording medium such as paper. The transfer system is not restricted to the embodiment as described above.

For example, a corotron can be used as the transfer apparatus for transferring a toner image from the latent image holding member onto paper etc. Although the corotron is effective as a unit of uniformly charging paper, a high-voltage power source is necessary for applying a high voltage of several kV for imparting the predetermined charge to paper employed as the recording medium. Since ozone is generated due to corona discharge, furthermore, rubber parts and the latent image holding member are deteriorated. It is therefore preferable to use a contact-transfer system in which an electroconductive transfer roll made of an elastic material is pressed against the latent image holding member to transfer the toner image onto paper. The transfer apparatus is not limited to the embodiment as described above.

<Cleaning Step>

The cleaning step is a step of removing the toner, paper powder, dust and debris, etc. adhering to the surface of the latent image holding member by directly contacting a blade, a brush, a roll or the like with the surface of the latent image holding member.

The most commonly used system is a blade cleaning system wherein a blade made of rubber such as polyurethane is pressed against the latent image holding member. On the other hand, use can be made of a magnetic brush system having a magnet fixed therein and being provided with a rotatable cylindrical non-magnetic sleeve arranged in the outer periphery of the magnet, wherein a magnetic carrier is carried on the surface of the sleeve to recover the toner, or a system wherein a semi-electroconductive resin fiber or animal hair is made rotatable in a rolled state, and bias of polarity opposite to the toner is applied to the roll to remove the toner. In the former magnetic brush system, a corotron for cleaning pretreatment may be provided. The cleaning system is not limited to the embodiment as described above.

<Fixation Step>

The fixation step is a step wherein the toner image transferred on the surface of the recording medium is fixed by using a fixation apparatus. As the fixation apparatus, it is preferable to use a heating fixation apparatus using a heat roll. The heating fixation apparatus includes a fixation roller having a heater lamp for heating that is arranged in a cylindrical metallic core and provided with a heat-resistant resin coating layer or a heat-resistant rubber coating layer as a release layer on the outer periphery thereof, and a press roller or a press belt being pressed against this fixation roller and having a heat-resistant elastic layer formed on the outer periphery of a cylindrical core or on the surface of a belt-shaped substrate.

In the step of fixing the toner image, the recording medium having the toner image formed thereon is passed between the fixation roller and the press roller or the press belt so that the binder resin, additives etc. in the toner are fixed by heat melting. However, the fixation step is not restricted to the embodiment as described above.

In the case of forming a full-color image, it is preferable to use the image forming method wherein plural latent image holding members have developer carriers in different colors, and by a series of steps consisting of the latent image forming step, the development step, the transfer step and the cleaning step with the respective latent image holding members and developer carriers, toner images in different colors are successively layered on the surface of the same recording medium. Then, the resulting layered full-color toner image is thermally fixed in the fixation step.

By using the developer of the exemplary embodiment in the image forming method as described above, stable development, transfer and fixation performance can be obtained even in a tandem system suitable for small-size and high-speed coloring.

<Latent Image Holding Member>

Next, the latent image holding member will be illustrated in detail.

Although a publicly known photoreceptor having at least a photosensitive layer on a conductive support is usable as the latent image holding member, it is preferable to use an organic photoreceptor therefor. In this case, it is preferable that the outermost layer of the latent image holding member (for example, a protective layer) contains a resin having a crosslinked structure. As the resin having a crosslinked structure, a phenol resin, a urethane resin, a siloxane-based resin, etc. are usable and a siloxane-based resin and a phenol-based resin are most preferred.

Because of having a high toughness, such a latent image holding member containing a resin having a crosslinked structure in the outermost layer is highly resistant to abrasion and scratches and, therefore, has a long life time.

In the case of using a cleaning blade as a unit for cleaning the latent image holding member to ensure good cleaning properties, however, the cleaning blade should be contacted with the latent image holding member under a relatively high contact pressure.

In this case, the toner remaining on the surface of the latent image holding member in the contact area between the cleaning blade and the latent image holding member is liable to be broken, which frequently causes adhesion of the toner components to the surface of the latent image holding member and a change in the charge accompanying the same. Because of having a high toughness, the toner of the exemplary embodiment can prevent filming even in this case. As a result, the change in the charge accompanying the filming can be also prevented.

The layer constitution of the latent image holding member is not particularly restricted, so long as it includes a conductive support and a photosensitive layer formed thereon. However, it is preferable that latent image holding member is of the function-separation type in which the photosensitive layer consists of a charge generating layer and a charge transporting layer. More specifically, it is preferable that the latent image holding member has a structure consisting of an undercoat layer, a charge generating layer, a charge transporting layer and a protective layer that are laminated in this order on the surface of a conductive support.

EXAMPLES

Next, the invention will be illustrated in greater detail by referring to Examples. However, it is to be understood that the invention is not restricted to the following Examples.

Unless otherwise noted, all "parts" and "percentages" in Examples are by weight.

(Methods of Measuring Various Characteristics)

First, methods that are used in Examples and Comparative Examples for measuring physical properties of the toners and so on will be illustrated.

<Molecular Weight of Resin>

The molecular weight distribution of a resin is determined by using an HLC-8120GPC, SC-8020 apparatus (manufactured by TOSOH CORPORATION), two TSK gel, Super HM-H columns (6.0 mm i.d.×15 cm), and THF (tetrahydrofuran) as an eluent. The measurement conditions are as follows: sample concentration: 0.5%; flow rate: 0.6 ml/min; sample injection amount: 10 µl; measuring temperature: 40° C.; and detector: an IR detector. A calibration curve is prepared from 10 samples (polystyrene standard samples TSK standard; manufactured by TOSOH CORPORATION) including A-500, F-1, F-10, F-80, F-380, A-2500, F-4, F-40, F-128, and F-700.

<Volume-average Particle Diameters of Resin Particles, Coloring Agent Particles, etc.>

The volume-average diameters of resin particles, coloring agent particles, etc. are measured by using a laser diffraction particle size measuring instrument (SALD2000A, manufactured by Shimadzu Corporation).

<Melting Temperature and Glass Transition Temperature of Resins>

The melting temperatures of a toner and a crystalline polyester resin and the glass transition temperatures of a toner and a non-crystalline resin are determined from maximum peaks that are measured according to ASTMD3418-8. Glass transition temperature is referred to the temperature at the intersection of the baseline and the rising line in an endothermic part, while melting temperature is referred to as the temperature at the top of an endothermic peak.

In the measurement, a differential scanning calorimeter (DSC60A provided with an automatic cooling device; manufactured by Shimadzu Corporation) is used.

(Production of Electrostatic Image Developer)

<Preparation of Binder Resin and Binder Resin Dispersion>

[Preparation of Non-crystalline Polyester Resin (A1) and Non-crystalline Resin Particle Dispersion (a1)]

| | |
|---|---|
| Polyoxyethylene (2,0)-2,2-bis(4-hydroxyphenyl)propane (bisphenol A ethylene oxide adduct) | 10 parts by mol |
| Polyoxypropylene (2,2)-2,2-bis(4-hydroxyphenyl)propane (bisphenol A propylene oxide adduct) | 90 parts by mol |
| Terephthalic acid | 10 parts by mol |
| Fumaric acid | 65 parts by mol |
| n-Octadecenylsuccinic acid | 5 parts by mol |
| Trimellitic acid | 20 parts by mol |
| Dibutyltin oxide | (0.05 part by mol relative to acid components (total number of moles of terephthalic acid, n-octadecenylsuccinic acid and trimellitic acid) |

The above components are charged in a two-necked flask having been dried by heating. After a nitrogen gas is introduced into the container to maintain an inert atmosphere, the mixture is heated so that condensation polymerization is conducted at 150° C. to 230° C. for 12 to 20 hours. Next, the pressure is gradually lowered at 210° C. to 250° C. to thereby synthesize a non-crystalline polyester resin (A1). The weight-average molecular weight Mw of this resin is 75,000 and its glass transition temperature Tg is 65° C.

| | |
|---|---|
| Non-crystalline polyester resin (A1) | 3,000 parts |
| Ion-exchanged water | 10,000 parts |
| Surfactant (sodium dodecyl benzene sulfonate) | 90 parts. |

The above components are charged in an emulsifying tank in a high-temperature/high pressure emulsifier (Cabitron CD1010, slit 0.4 mm). After melting the mixture by heating to 130° C., it is dispersed at 110° C. in a flow rate of 3 L/m at 10,000 rpm for 30 minutes and passed through a cooling tank. Thus, a non-crystalline resin particle dispersion (high temperature/high pressure emulsifier (Cabitron CD1010, slit 0.4 mm)) is collected to give anon-crystalline resin particle dispersion (a1).

[Preparation of Non-crystalline Polyester Resin (B1) and Non-crystalline Resin Particle Dispersion (B1)]

A non-crystalline polyester resin (B1) is prepared under the same conditions as for the non-crystalline polyester resin (A1) but adding no trimellitic acid and changing the amounts of polyoxyethylene (2,0)-2,2-bis(4-hydroxyphenyl)propane and polyoxypropylene (2,2)-2,2-bis(4-hydroxyphenyl)propane respectively to 40 parts by mol and 60 parts by mol. The weight-average molecular weight Mw of this resin is 35,000 and its glass transition temperature Tg is 55° C. Subsequently, a non-crystalline resin particle dispersion (b1) is obtained under the same conditions as for the non-crystalline resin particle dispersion (a1).

[Preparation of Crystalline Polyester Resin (C1) and Crystalline Resin Particle Dispersion (C1)]

| | |
|---|---|
| 1,9-Nonanediol | 44 parts by mol |
| Dodecanedicarboxylic acid | 56 parts by mol |
| Dibutyltin oxide | 0.05 parts by mol. |

The above components are charged in a three-necked flask having been dried by heating. After a nitrogen gas is introduced into the container to maintain an inert atmosphere, the mixture is mechanically stirred at 180° C. for 2 hours. Next, it is gradually heated to 230° C. under reduced pressure and stirred for 5 hours. When the mixture becomes viscous, the reaction is ceased by cooling. Thus, a crystalline polyester resin (C1) is synthesized. The weight-average molecular weight Mw of this resin is 35,000 and its melting temperature Tm is 75° C.

Subsequently, a crystalline resin particle dispersion (c1) is obtained under the same conditions as for the preparation of the non-crystalline resin particle dispersion (a1) using a high temperature/high pressure emulsifier (Cabitron CD1010, slit 0.4 mm).

<Preparation of Coloring Agent Particle Dispersions>

[Preparation of Coloring Agent Particle Dispersion (1)]

| | |
|---|---|
| Magenta pigment (PR57.1 FUJICARMINE 6B; manufactured by Fuji Pigment Co., Ltd.) | 35 parts |
| Anionic surfactant (EMUL 20C (Na salt of polyoxyethylene lauryl ether sulfate; manufactured by Kao Corp.) | 2 parts |
| Ion-exchanged water | 125 parts |

The above components are mixed and dissolved. Next, the coloring agent is dispersed by using a high-impact type dispersion machine Ultimizer (HJP 30006; manufactured by Sugino Machine Limited) for 1 hour to give a coloring agent particle dispersion (1). The volume-average particle diameter of the coloring agent in the coloring agent particle dispersion (1) is 0.12 μm and the coloring agent particle concentration is 21% by weight. The ratio of coarse particles having a volume-average particle diameter of 0.8 μm or more contained in the coloring agent particle dispersion is 2% by number.

[Preparation of Coloring Agent Particle Dispersion (2)]

| | |
|---|---|
| Yellow pigment (PY75 Sico Yellow FR1252; manufactured BASF) | 35 parts |
| Anionic surfactant (EMUL 20C; manufactured by Kao Corp.) | 2 parts |
| Ion-exchanged water | 125 parts |

The above components are mixed and dissolved. Next, the coloring agent is dispersed by using a high-impact type dispersion machine Ultimizer (HJP 30006; manufactured by Sugino Machine Limited) for 1 hour to give a coloring agent particle dispersion (2). The volume-average particle diameter of the coloring agent in the coloring agent particle dispersion (2) is 0.15 μm and the coloring agent particle concentration is 20% by weight. The ratio of coarse particles having a volume-average particle diameter of 0.8 μm or more contained in the coloring agent particle dispersion is 2.5% by number.

<Preparation of Mold Releasing Agent Particle Dispersion (1)>

| | |
|---|---|
| Ketone wax (stearyl ketone; manufactured by Kao Corp.) | 100 parts |
| Anionic surfactant (Newlex Paste R; manufactured by NOF Corp.) | 2 parts |
| Ion-exchanged water | 300 parts |

The above components are heated to 95° C. and then dispersed by using a homogenizer (Ultra-Turrax T50; manufactured by IKA Corp.). Next, it is further dispersed by using a pressure discharge type Gorlin homogenizer (manufactured by Gorlin Co., Ltd.) to give a mold releasing agent particle dispersion (1) in which mold releasing agent particles having a volume-average particle diameter of 200 nm are dispersed (mold releasing agent concentration: 24% by weight).

<Production of Toner>

[Production of Toner A1]

| | |
|---|---|
| Non-crystalline resin particle dispersion (a1) | 160 parts |
| Non-crystalline resin particle dispersion (b1) | 160 parts |
| Crystalline resin particle dispersion (c1) | 80 parts |
| Coloring agent particle dispersion (1) | 50 parts |
| Mold releasing agent particle dispersion | 60 parts |
| Aluminum sulfate (manufactured by Wako Pure Chemical Industries, Ltd.) | 5 parts |
| Aqueous solution of surfactant (NEO-PEREX GP25; manufactured by KAO Corp., 25% aq. solution) | 5 parts |
| 0.3 M aqueous solution of nitric acid | 50 parts |
| Ion-exchanged water | 500 parts |
| 10% aqueous HEDP solution (PH212; manufactured by CHELEST) | 3 parts |

Among the above components, the 10% aqueous HEDP solution and the coloring agent particle dispersion are mixed by stirring, heated in a water bath at 40° C., held at that temperature for 30 minutes and then cooled to thereby give a coloring agent dispersion mixture.

Next, the coloring agent dispersion mixture and the other components as described above are fed into a round bottom stainless flask. After dispersing by using a homogenizer (Ultra-Turrax T50; manufactured by IKA Corp.), it is heated to 45° C. in a heating oil bath under stirring. After maintaining at 48° C. and confirming the formation of aggregated particles having an average particle diameter of about 4.8 μm, a resin particle dispersion mixture consisting of 50 parts of the non-crystalline resin particle dispersion (a1) and 50 parts of the non-crystalline resin particle dispersion (b1) is additionally added and the mixture is maintained for 30 minutes.

Subsequently, 0.5 parts of 10% aqueous HEDP solution is further added and a 1N aqueous sodium hydroxide solution is gently added until the pH value attains 7.0. While continuing stirring, the mixture is heated to a definite temperature (90° C.) and maintained for a definite period of time. Next, the reaction product is filtered, washed with ion-exchanged water and then dried by using a vacuum dryer to give toner mother particles.

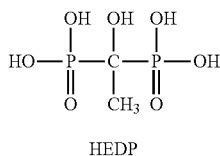

HEDP

[Treatment with External Additive]

Then, 1.5 parts of titania (STR 60-C-LP; manufactured by SAKAI CHEMICAL INDUSTRY, Co., Ltd.) is mixed by using a Henschel mixer and externally added to the toner mother particles obtained above to give toner A1.

[Production of Toner A2]

Toner A2 is obtained under the same conditions as for toner A1 but using the coloring agent particle dispersion (2) as a substitute for the coloring agent particle dispersion (1)

[Production of Toner A3]

Toner A3 is obtained under the same conditions as for toner A1 but using a 10% aqueous solution of PBTC (PH430; manufactured by CHELEST) as a substitute for the 10% aqueous solution of HEDP (PH212; manufactured by CHELEST).

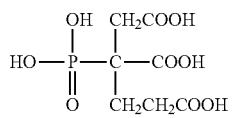

PBTC (Phosphonobutane Tricarboxylic Acid)

[Production of Toner A4]

Toner A4 is obtained under the same conditions as for toner A1 but changing the addition amount of the 10% aqueous solution of HEDP (PH212; manufactured by CHELEST) from 3 parts to 10 parts.

[Production of Toner A5]

Toner A5 is obtained under the same conditions as for toner A1 but changing the addition amount of the 10% aqueous solution of HEDP (PH212; manufactured by CHELEST) from 3 parts to 0.2 parts.

[Production of Toner A6]

Toner A6 is obtained under the same conditions as for toner A1 but not adding 10% aqueous solution of HEDP (PH212; manufactured by CHELEST).

[Production of Toner A7]

Toner A7 is obtained under the same conditions as for toner A1 but using a 10% alkyl phosphate-based surfactant (ADEKA COL PC; manufactured by ADEKA Corp.) as a substitute for 10% aqueous solution of HEDP (PH212; manufactured by CHELEST).

[Production of Toner A8]

Toner A8 is obtained under the same conditions as for toner A7 but the step of adding the 10% alkyl phosphate-based surfactant (ADEKA COL PC; manufactured by ADEKA Corp.) to the coloring agent particle dispersion is omitted and, as a substitute therefor, the 10% alkyl phosphate-based surfactant is added following the step wherein, after the completion of the aggregation step, the 1N aqueous sodium hydroxide solution is gently added until the pH value attains 7.0.

<Production of Developer>
[Production of Developer A1]
<Production of Carrier>

1,000 parts of Mn—Mg ferrite (volume average particle diameter 50 µm; manufactured by POWDERTEC) is fed into a kneader. Then, a solution prepared by dissolving 150 parts of a styrene-methyl methacrylate copolymer (polymerization ratio 40:60, Tg 90° C., weight-average molecular weight 72,000; manufactured by Soken Chemical & Engineering Co., Ltd.) in 700 parts of toluene is added thereto. After mixing at room temperature for 20 minutes, the mixture is heated to 70° C. and dried under reduced pressure. Then, the residue is taken out to give a coat carrier. The coat carrier thus obtained is passed through a 75 µm-sieve and coarse particles are removed to give a carrier. This carrier and the toner are fed into a V-type blender at a weight ratio of 95:5 and stirred for 20 minutes. Thus, developer A1 is obtained.

[Production of Developers A2 to A8]

Developers A2 to A8 are produced as in the developer A1 but using the toners A2 to A8 as a substitute for the toner A1.

(Production of Latent Image Holding Member)

A cylindrical Al substrate (cylinder) is polished with a center-less polishing apparatus to such an extent that the surface roughness Rz attains 0.6 µm. In the cleaning step, this cylinder is degreased, then etched for 1 minute in a 2% by weight aqueous solution of sodium hydroxide, neutralized and washed with purified water. Next, it is subjected to an anodizing treatment to form an anodized film (current density 1.0 A/dm$^2$) on the surface of the cylinder by using a 10% by weight sulfuric acid solution. After washing with water, the anodized film is subjected to pore sealing by dipping in a 1% by weight nickel acetate solution at 80° C. for 20 minutes, followed by washing with purified water and drying. Thus, a 7 µm anodized film is formed on the surface of the aluminum cylinder.

One part of titanyl phthalocyanine having a strong diffraction peak at a Bragg angle (2θ±0.2°) of 27.2° in an x-ray diffraction spectrum is mixed with 1 part of polyvinyl butyral (SEREK BM-S, manufactured by SEKISUI CHEMICAL CO., LTD.) and 100 parts of n-butyl acetate and dispersed together with glass beads in a paint shaker for 1 hour, and the resulting coating solution is applied by dip-coating on the undercoat layer on the aluminum substrate described above. After drying by heating at 100° C. for 10 minutes, a charge generating layer of 0.15 µm in thickness is formed.

Next, a coating solution prepared by dissolving 2 parts of a benzidine compound having the following structure (the following compound 1) and 2.5 parts of a polymer compound (the following compound 2, viscosity-average molecular weight: 39,000) in 20 parts of chlorobenzene is applied by dip-coating on the charge generating layer. After heating at 110° C. for 40 minutes, a charge transporting layer of 20 µm in thickness is formed.

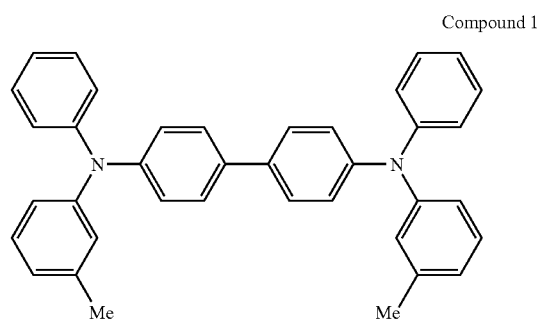

Compound 1

-continued

Compound 2

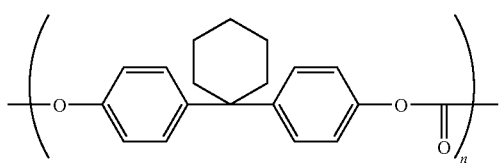

Five parts of the following compound 4.7 parts of resol type phenol resin (PL-4852; manufactured by Gunei Chemical Industry Co., Ltd.), 0.03 parts of methylphenyl polysiloxane, 5 parts of fine $CaCO_3$ particles (CCR, average particle diameter: 0.1 μm; manufactured by SHIRAISHI CALCIUM) and 20 parts of isopropanol are mixed and dissolved to give a coating solution for forming protective layer. This coating solution for forming protective layer is applied on the electron transporting layer of the latent image holding member as described above by dip-coating, and dried at 130° C. for 40 minutes. Thus, a protective layer of 3 μm in thickness is formed and thereby a latent image holding member is obtained.

Compound 4

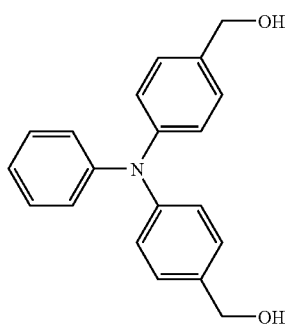

(Evaluation)
<Latent Image Holding Member Surface Conditions and Cleaning Blade Conditions>

By using a modified apparatus of Printer Docu Centre Color 400CP (manufactured by Fuji Xerox Co., Ltd.), a photoreceptor and a developer are combined and used in an image forming test (image coverage density 5%) on 100,000 sheets in a high-temperature and high-humidity (28° C., 85% RH) environment and then in another image forming test on 100,000 sheets in a low-temperature and low-humidity (10° C., 15% RH) environment. Then, the latent image holding member surface conditions and changes in the cleaning blade are evaluated. The latent image holding member surface conditions are observed through a glass (50× magnification) while the changes in the blade are observed under a laser microscope (100× magnification).

Latent image holding member surface conditions:
  A: Neither adhesion nor filming observed under the glass.
  B: Faint adhesion observed in the peripheral direction of the glass, though invisible in image.
  C: Somewhat practically problematic because of having small scratches on the surface and unevenness in image density.
  D: Practically pragmatic because of having image defects and scratches.
Cleaning blade conditions:
  A: Excellent and no abrasion observed both in image area and non-image area.
  B: Practically not problematic, though difference observed between image area and non-image area.
  C: Problematic in some cases depending on image density because of suffering from serious abrasion in image area.
  D: Problematic because of causing cleaning failure and streaking in image.

The evaluation results are as follows.
<Ratio of the Intensity of Phosphorus Element to the Total Intensity of all Elements Detected in the Toner by the Fluorescent X-ray Analysis (A)>

The ratio of the intensity (A) of phosphorus element to the total intensity of all elements detected in the toner by the fluorescent X-ray analysis is measured in the following manner.

From the obtained toner, the external additive is removed by air-blowing in a gauge and the mother particles are collected. Then, these particles are subjected to the measurement in vacuo (degree of vacuum: 10 to 100 Pa) in a PR gas ($Ar+CH_4$) atmosphere at an accelerating voltage of 40 kV and at an electrical current value of 70 mV for a measurement time of 15 minutes. The fluorescent X-ray analysis is conducted using a fluorescent X-ray analyzer XRS1500 (produced by Shimadzu Corp.).

The ratio of the intensity of phosphorus element to the total intensity of all elements detected is calculated and referred to as A.
<Ratio of the Intensity of Phosphorus Element to the Total Intensity of all Elements Detected in the Toner by the Fluorescent X-ray Analysis Conducted after Dispersing Toner Particles in an Alcoholic Solvent and Drying (B)>

The ratio of the intensity (B) of phosphorus element to the total intensity of all elements detected in the toner, in which toner particles have been dispersed in an alcoholic solvent followed by drying, by the fluorescent X-ray analysis is measured in the following manner.

After dispersing 5 g of the obtained toner in 100 ml of a solvent mixture (water+ethanol, ratio by volume 50:50), the toner is dispersed by stirring with an ultrasonic dispersion machine at a temperature of 20 to 30° C. using a three one motor for 10 minutes. After filtering and drying, a toner is obtained. The dried tone is subjected to the fluorescent X-ray analysis in the same manner as for A. Thus, the ratio of the intensity of phosphorus element to the total intensity of all elements detected in the toner by the fluorescent X-ray analysis (B) is determined.

From the measurement results on (A) and (B) thus obtained, (B/A) is calculated.

The (A) and (B/A) values thus obtained are as follows.
<Average Circularity and Number-average Particle Diameter>

The average circularity of the obtained toner is measured by using a flow-type particle image analyzer FPIA-2000 (manufactured by Sysmex Corp.). In the measurement, 4±1 mg of the toner is added to 2 ml of a 5% by weight aqueous sodium alkylbenzenesulfonate solution employed as a dispersant and then the resultant mixture is added to 40 ml of an electrolyte. The number of the particles measured is within the range of 3,500±1,000. From the data of the all particles obtained, the particle diameter range of 0.5 times or more but not more than 0.7 times larger than the number-average particle diameter is extracted and the average is calculated.

The number-average particle diameter is measured by using a Multisizer II (manufactured by Beckman Coulter, Inc.) and an electrolyte ISOTON-II (manufactured by Beckman Coulter, Inc.). In the measurement, 5±1 mg of the toner is added to 2 ml of a 5% by weight aqueous sodium alkylbenzenesulfonate solution employed as a dispersant and then the resultant mixture is added to 30 ml of an electrolyte.

The suspension having the sample dispersed therein is dispersed by using an ultrasonic dispersion machine and then the particle size distribution of particles having a diameter or 2 μm or more but not more than 50 μm is measured by using the Multisizer II as described above with the use of a 100 μm aperture as the aperture diameter.

The results are as follows.

TABLE 1

|  | Example 1 | Example 2 | Example 3 | Example 4 | Example 5 | Comp. Example 1 | Comp. Example 2 | Comp. Example 3 |
|---|---|---|---|---|---|---|---|---|
| Toner/developer | A1 | A2 | A3 | A4 | A5 | A6 | A7 | A8 |
| A | 0.12 | 0.2 | 0.18 | 0.48 | 0.08 | 0 | 0.52 | 0.08 |
| B/A | 0.48 | 0.55 | 0.41 | 0.68 | 0.73 | — | 0.37 | 0.8 |
| Average circularity | 0.965 | 0.979 | 0.951 | 0.962 | 0.959 | 0.949 | 0.981 | 0.968 |
| Number ratio (%) of particles having circularity of 0.940-0.970 within particle diameter range of 0.5-0.7 times larger than number-average particle diameter | 3.5 | 3.2 | 4 | 1.8 | 14 | 16 | 17 | 17.5 |
| Image holding member conditions | A | A | A | B | B | D | D | C |
| Cleaning blade conditions | A | A | A | A | B | C | C | D |

What is claimed is:

1. An electrostatic-image-developing toner, which is obtained by:
adding a phosphonic acid based sequestering agent in a particle dispersion, and then
being subject to aggregation,
wherein the phosphonic acid based sequestering agent comprises at least one of a compound represented by the following formula (1) and a compound represented by the following formula (2):

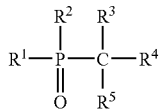

(1)

wherein each of $R^1$ and $R^2$ represents —OM, wherein M represents a hydrogen atom, an alkali metal or a quaternary ammonium;
each of $R^3$, $R^4$ and $R^5$ independently represents a hydroxyl group, a carboxyl group, an alkyl or alkenyl group optionally having a hydroxyl or carboxyl group at the terminal thereof, or $NR^{12}R^{13}$, wherein each of $R^{12}$ and $R^{13}$ independently represents a hydrogen atom, an alkyl group, an alkenyl group or an acyl group, and $R^{12}$ and $R^{13}$ may be bonded together to form a ring; and
$R^1$ and $R^2$ may be the same as or different from each other,

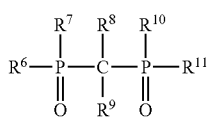

(2)

wherein each of $R^6$, $R^7$, $R^{10}$ and $R^{11}$ represents —OM, wherein M represents a hydrogen atom, an alkali metal or a quaternary ammonium;
each of $R^8$ and $R^9$ independently represents a hydrogen atom, a hydroxyl group, an alkyl group, an alkenyl group or $NR^{12}R^{13}$, wherein each of $R^{12}$ and $R^{13}$ independently represents a hydrogen atom, an alkyl group, an alkenyl group or an acyl group, and $R^{12}$ and $R^{13}$ may be bonded together to form a ring; and $R^6$, $R^7$, $R^{10}$ and $R^{11}$ may be the same as or different from each other, and
wherein the following requirements are satisfied:

$$0.05 \leq A \leq 0.5$$

$$0.40 \leq B/A \leq 0.75$$

wherein A represents a ratio of an intensity of phosphorus element to a total intensity of all elements detected in the toner by the fluorescent X-ray analysis, and
B represents a ratio of an intensity of phosphorus element to a total intensity of all elements detected in a toner having been dispersed in an alcoholic solvent and followed by drying, by the fluorescent X-ray analysis.

2. The electrostatic-image-developing toner according to claim 1, further comprising:
at least one of a mold releasing agent and a coloring agent.

3. The electrostatic-image-developing toner according to claim 1, wherein
an average circularity the toner is from about 0.950 to about 0.980, and
a number ratio of particles having circularity of 0.980 or less within a particle diameter range of from 0.5 times to 0.7 times larger than a number-average particle diameter is from about 1.5% to about 15.5%.

4. An electrostatic image developer comprising:
the electrostatic-image-developing toner according to claim 1; and
a carrier.

5. A method of producing the electrostatic-image-developing toner according to claim 1, comprising:
dispersing at least one of a coloring agent and a mold releasing agent to give at least one of a coloring agent dispersion and a mold releasing agent dispersion;
mixing the phosphonic acid based sequestering agent with at least one of the coloring agent dispersion and the mold releasing agent dispersion to give a phosphonic acid based sequestering agent mixture dispersion; and
mixing the phosphoric acid based sequestering agent mixture dispersion with a resin particle dispersion to aggregate and fuse the dispersed substances.

6. An image forming method comprising:
forming an electrostatic latent image on a surface of a latent image holding member;
developing the electrostatic latent image formed on the surface of the latent image holding member with a developer comprising a toner to form a toner image;
transferring the toner image formed on the surface of the latent image holding member to a surface of a transfer-receiving material; and fixing the toner image transferred on the surface of the transfer-receiving material;
wherein
the toner is the electrostatic-image-developing toner according to claim 1.

7. An image forming apparatus comprising:

a latent image holding member;

a charging unit that charges the latent image holding member;

an exposing unit that exposes the latent image holding member to form an electrostatic latent image on the latent image holding member;

a development unit that develops the electrostatic latent image with a developer to form a toner image; and a transfer unit that transfers the toner image on the latent image holding member to a recording material;

wherein the developer comprises the electrostatic-image-developing toner according to claim 1.

* * * * *